(12) United States Patent
Ohkawa et al.

(10) Patent No.: US 7,750,037 B2
(45) Date of Patent: Jul. 6, 2010

(54) ANTIDEPRESSANT

(75) Inventors: Shigenori Ohkawa, Takatsuki (JP); Masaomi Miyamoto, Takarazuka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 178 days.

(21) Appl. No.: 11/475,539

(22) Filed: Jun. 27, 2006

(65) Prior Publication Data

US 2006/0241168 A1  Oct. 26, 2006

Related U.S. Application Data

(62) Division of application No. 10/506,269, filed as application No. PCT/JP03/02293 on Feb. 28, 2003, now abandoned.

(30) Foreign Application Priority Data

Mar. 1, 2002 (JP) ............... 2002-055771
Jul. 4, 2002 (JP) ............... 2002-195434

(51) Int. Cl.
A61K 31/4035 (2006.01)
C07D 405/02 (2006.01)

(52) U.S. Cl. .................. 514/414; 548/414

(58) Field of Classification Search ............ None
See application file for complete search history.

(56) References Cited

U.S. PATENT DOCUMENTS

| 5,266,707 | A | 11/1993 | Matsumoto et al. |
| 6,479,536 | B1 | 11/2002 | Ohkawa et al. |
| 6,878,831 | B2 | 4/2005 | Aoki et al. |
| 7,153,871 | B2 * | 12/2006 | Schumacher et al. ........ 514/337 |
| 2001/0026796 | A1 | 10/2001 | Croce et al. |
| 2002/0160996 | A1 | 10/2002 | Ohkawa et al. |
| 2004/0034049 | A1 | 2/2004 | Okawa et al. |
| 2004/0167171 | A1 | 8/2004 | Ohkawa et al. |
| 2005/0187238 | A1 | 8/2005 | Ohkawa et al. |

FOREIGN PATENT DOCUMENTS

| EP | 1 136 477 | 9/2001 |
| JP | 1 149765 | 6/1989 |
| JP | 11-049765 | 2/1999 |
| JP | 2002-201172 | * 7/2002 |
| JP | 2002-348239 | 12/2002 |
| WO | WO 98/55454 | 12/1998 |
| WO | WO 00/21927 | 4/2000 |
| WO | WO 00/34262 | 6/2000 |
| WO | WO 02/22862 | 3/2002 |
| WO | WO 02/28850 | 4/2002 |
| WO | WO 02/053551 | 7/2002 |
| WO | WO 03/000646 | * 1/2003 |
| WO | WO 03/004485 | 1/2003 |

OTHER PUBLICATIONS

Machine Translation of JP 2002-201172, Jul. 16, 2002.*
Ohaeri, J. U., "Naturalistic Study of Olanzapine in Treatment-Resistant Schizophrenia and Acute Mania, Depression and Obsessional Disorder", East African Medical Journal, 77(2), 86-92, Feb. 2000, file Medline on STN, Abstract No. 2000235896, 2000.*
Bourgery, G., et al., "Synthesis and Antiarrhythmic Activity of New Benzofuran Derivatives", Journal of Medicinal Chemistry, (1981), vol. 24, No. 2, pp. 159-167.
Erlenmeyer, H., et al., " 13. Zur Kenntnis des 5-Aminocumarons", Helvetica Chimica Acta, (1948), vol. 31, pp. 75-77.
Snow, R.E., et al. "Psychosis in Neurodegenerative Disease," Semin Clin. Neuropsychiatry, vol. 4, pgs. 282-293 (1996) (abstract only).
Bryan L. Roth, "Neuronal Signal Transduction Pathways: Wasteland or the Promised Land," SCI. STKE, vol. 2000(45), p. PE1 (2000). (4 pages).
Wolozin, B., et al., "Mechanisms of Neurodegenerative Disorders," Arch Neurol., vol. 57, pp. 801-804 (2000).

(Continued)

Primary Examiner—Fiona T Powers
(74) Attorney, Agent, or Firm—Edwards Angell Palmer & Dodge LLP; David G. Conlin; Mark D. Russett

(57) ABSTRACT

A PKB (Akt) activating agent comprising a compound represented by the formula (I):

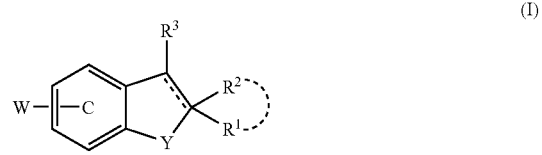

wherein $R^1$ and $R^2$: H, a hydrocarbon group or a heterocyclic group or $R^1$ and $R^2$ form a ring in cooperation with the adjacent carbon atom; $R^3$: H, a hydrocarbon group or a heterocyclic group; W: represents a group represented by the formulas:

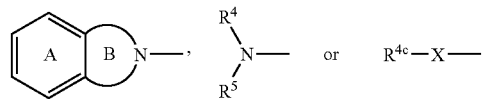

wherein ring A: an optionally substituted benzene ring; ring B: an optionally substituted 5- to 7-membered nitrogen-containing heterocycle; $R^4$: an aliphatic hydrocarbon group substituted with an aromatic group and further optionally substituted, or an acyl group containing an aromatic group; $R^5$: H, $C_{1-6}$ alkyl or acyl; $R^{4c}$: an aromatic group, an aliphatic hydrocarbon group or acyl; and X: O or S; Y: O, S or NH; and ring C: an optionally substituted benzene ring, or a salt or a prodrug thereof, and use of the activating agent in prevention or treatment of depression, anxiety, manic-depressive psychosis or PTSD are provided.

1 Claim, 1 Drawing Sheet

OTHER PUBLICATIONS

European examination report dated Mar. 11, 2008, in corresponding EPO Application No. 03707169.3.

Chalecka-Franaszek et al., "Lithium activates the serine/threonine kinase Akt-1 and suppresses glutamate-induced inhibition of Akt-1 activity in neurons", Proc. Natl. Acad. Sci. USA, vol. 96, pp. 8745-8750, Jul. 1999.

Chinese Office Action dated May 15, 2009 in corresponding Chinese patent application No. 03804872.8 (with English translation).

Nestler, "Antidepressant Treatments in the 21st Century", Biol Psychiatry (1998) 44:526-533.

Wierońska et al., "Metabotropic glutamate receptors in the tripartite synapse as a target for new psychotropic drugs", Neurochemistry International 55 (2009) 85-97.

Beaulieu, et al., "An Akt/β-Arrestin 2/PP2A Signaling Complex Mediates Dopaminergic Neurotransmission and Behavior", Cell vol. 122, 261-273, Jul. 29, 2005.

Japanese Office Action dated Jul. 28, 2009 in corresponding Japanese patent application No. 2003-052503 (with English translation).

* cited by examiner

ANTIDEPRESSANT

This application is a divisional of U.S. patent application Ser. No. 10/506,269, abandoned, which was the National Phase filing of International Patent Application No. PCT/JP03/02293, filed Feb. 28, 2003.

TECHNICAL FIELD

The present invention relates to protein kinase B (hereinafter, referred to as PKB in some cases) activating agents and use of these PKB activating agents for preventing or treating depression, PTSD, Parkinson's disease, Alzheimer's diseases, and the like.

BACKGROUND ART

Protein kinase B (PKB) is also referred to as Akt, is one of protein phosphorylases, transmits stimuli from the extracellular to the inside of a cell, and is known to be involved in response of a cell to these stimuli. In particular, it is suggested that a signal transduction from phosphatidylinositol-3 (hereinafter, referred to as PI-3) is involved in nerve cell survival, nerve regeneration or nerve differentiation. Further, a method of treating diseases such as diabetes with an inhibitor of glycogen synthase kinase-3β (hereinafter, referred to as GSK in some cases) which is one of substrates of PKB is also known. However, PKB activation and effects of treating neurodegenerative diseases such as Parkinson's disease are not necessarily confirmed in vitro. In addition, a relationship between PKB activation and effects of preventing or treating depression, anxiety, manic-depressive psychosis or PTSD (posttraumatic stress disorder; hereinafter, abbreviated as PTSD in some cases) is not confirmed.

On the other hand, as a disease in which neurodegenerative disease, that is, selective nerve cell death occurs progressively, Alzheimer's diseases, Parkinson's disease, amyotrophic lateral sclerosis (ALS) and Huntington's disease are known.

As current drug therapy, replacement therapy of making up for depletion of a neurotransmitter accompanied with neurodegeneration is prevailing and, regarding Parkinson's disease, a dopamine agonist such as L-dopa which is a precursor of dopamine is used as a replacement therapeutic agent or a symptomatic therapeutic agent. However, those replacement therapeutic agent and symptomatic therapeutic agent do not suppress progression of neurodegeneration, and effects are gradually lost with disease progression. For this reason, exploitation of drugs which suppress progression of neurodegeneration and promote regeneration of remaining nerve ending is desired, but drugs having such the activity have not been found out. Further, in neurodegenerative diseases, it is considered that a majority of nerve cells are degenerated at sideration, and it is thought that only degeneration suppression or promotion of regeneration of nerve ending can not regenerate sufficient function.

On the other hand, recently, great concept conversion has occurred regarding ability to regenerate a central nervous system. Previously, it has been thought that when neurodegeneration occurs in a central nervous system, recovery of function is difficult since nerve is not newly produced and replenished. However, it has been most recently and continuously revealed that a nerve stem cell and a nerve precursor cell which can newly produce a nerve are present in a central nervous system of a mature mammal including a human being, and study of possibility of regenerating disordered nerve tissue and function by activating an endogenous nerve stem cell has been initiated [see Nature Medicine, vol. 4, p. 1313-1317, 1998 and Nature Medicine, vol. 6, p. 271-277, 2000].

Benzofuran derivatives which have nerve regeneration promoting activity and are useful as a medicine for preventing or treating nerve degeneration diseases are reported in WO98/55454 and WO 00/34262.

OBJECTS OF THE INVENTION

One object of the present invention is to provide a medicine for preventing or treating Parkinson's diseases and the like by promoting nerve regeneration and maintaining survival of a nerve cell including fundamental nerve neogenesis, not by mere replacement therapy or symptomatic therapy. Another object of the present invention is to provide a PKB activating agent which is suitable for achieving such the object. In addition, although many of patients suffering from depression, anxiety and manic-depressive psychosis in present stress society greatly need remedies, previous antidepressants are insufficient in therapeutic effect, and side effect often becomes problematic and, therefore, remedies for depression which have higher therapeutic efficacy are demanded. In addition, also regarding PTSD (posttraumatic stress disorder) which is also diseases based on stress, drugs which have fewer side effect, and have higher preventing or treating efficacy are demanded. Another object of the present invention is to provide an agent for preventing or treating depression, anxiety, manic-depressive psychosis and PTSD (posttraumatic stress disorder) which has low side effect, and has new different action of mechanism from the previously known monoamine inhibitory activity, selective serotonin reuptake inhibitory activity, and cortisol synthesis inhibitory activity.

DISCLOSURE OF THE INVENTION

In order to achieve the above objects, the present inventors intensively studied drugs which exert actions or effects of nerve regeneration, nerve neogenesis, and nerve survival maintenance together with clarification of action of mechanism and, as the result, found that the compound represented by the following formula (I) has excellent PKB activating activity, and further found out that compounds having the PKB activating activity can be a useful drug for preventing or treating Parkinson's diseases, by promoting nerve regeneration, and maintaining/protecting survival of a nerve cell, including nerve neogenesis.

In addition, the present inventors intensively researched an agent for preventing or treating depression, anxiety, manic-depressive psychosis and PTSD (posttraumatic stress disorder; hereinafter, abbreviated as PTSD in some cases) due to different mechanism from the previous action of mechanism and, as a result, found out that a PKB activating agent, in particular, a nerve regeneration promoting agent and/or a nerve stem cell or nerve precursor cell differentiation promoting agent due to PKB activation are unexpectedly effective in treating or preventing these diseases, inter alia, the following benzofuran derivative is effective in treating or preventing them as such the nerve regeneration promoting agent, and further continued to study, which resulted in completion of the present invention.

That is, the present invention relates to:

(1) A protein kinase B (PKB) activating agent, which comprises a compound represented by the formula:

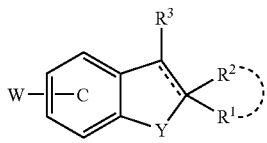

(I)

wherein R¹ and R² may be the same or different, and represent a hydrogen atom, an optionally substituted hydrocarbon group or an optionally substituted heterocyclic group, or R¹ and R² may be taken together with the adjacent carbon atom to form an optionally substituted 3- to 8-membered homocycle or heterocycle, R³ represents a hydrogen atom, an optionally substituted hydrocarbon group or an optionally substituted heterocyclic group, ═══ represents a single bond or a double bond, W is (i) a group represented by the formula:

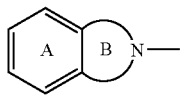

(Wa)

wherein the A ring represents an optionally substituted benzene ring and the B ring represents an optionally substituted 5- to 7-membered nitrogen-containing heterocycle, (ii) a group represented by the formula:

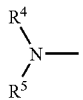

(Wb)

wherein $R^4$ represents (1) an aliphatic hydrocarbon group substituted with an optionally substituted aromatic group and optionally further substituted, or (2) an acyl group containing an optionally substituted aromatic group, and $R^5$ represents a hydrogen atom, $C_{1-6}$ alkyl or an acyl group, or (iii) a group represented by the formula:

$R^{4c}$—X—  (Wc)

wherein $R^{4c}$ represents an optionally substituted aromatic group, an optionally substituted aliphatic hydrocarbon group, or an acyl group, and X represents an oxygen atom or an optionally oxidized sulfur atom, Y represents an oxygen atom, an optionally oxidized sulfur atom, or optionally substituted imino, and the C ring represents a benzene ring which may be further substituted in addition to a group represented by W, or a salt thereof, or a prodrug thereof;

(2) The agent according to (1), wherein ═══ is a single bond;

(3) The agent according to (1), wherein Y is an oxygen atom;

(4) The agent according to (1), wherein W is a group represented by the formula (Wa);

(5) The agent according to (1), wherein R¹ and R² are each a $C_{1-6}$ alkyl group, R³ is a phenyl group optionally substituted with 1 to 3 substituents selected from $C_{1-6}$ alkyl and halogen, the C ring is a benzene ring optionally substituted with 1 to 3 substituents selected from $C_{1-6}$ alkyl and $C_{1-6}$ alkoxy, ═══ is a single bond, Y is an oxygen atom, W is a group represented by (Wa), and a group represented by the formula (Wa) is a group represented by the formula:

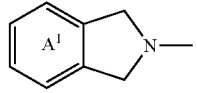

wherein an $A^1$ ring represents a benzene ring optionally substituted with 1 to 3 substituents selected from halogen, $C_{1-6}$ alkoxy and $C_{1-6}$ alkylenedioxy;

(6) The agent according to (1), wherein the 5-position of the benzofuran ring is substituted with a group represented by the formula (Wa);

(7) The agent according to (1), which comprises [1] 2-[2,2,4,6,7-pentamethyl-3-(4-methylphenyl)-2,3-dihydro-1-benzofuran-5-yl]isoindoline, [2] 5,6-dimethoxy-2-[2,2,4,6,7-pentamethyl-3-(4-methylphenyl)-2,3-dihydro-1-benzofuran-5-yl]isoindoline, [3] 5,6-dimethoxy-2-[3-(4-isopropylphenyl)-2,2,4,6,7-pentamethyl-2,3-dihydro-1-benzofuran-5-yl]isoindoline, [4] 5,6-dimethoxy-2-[2,2,4,6,7-pentamethyl-3-(4-methylphenyl)-2,3-dihydro-1-benzofuran-5-yl]-2H-isoindole, [5] 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole, [6] 6-[2,2,4,6,7-pentamethyl-3-(4-methylphenyl)-2,3-dihydro-1-benzofuran-5-yl]-6H-[1,3]dioxolo[4,5-f]isoindole, [7] 6-(2,2,4,6,7-pentamethyl-3-phenyl-2,3-dihydro-1-benzofuran-5-yl)-6,7-dihydro-5H-[1,3]dioxolo[4,5-f]isoindole, [8] (R)-5,6-dimethoxy-2-[2,2,4,6,7-pentamethyl-3-(4-methylphenyl)-2,3-dihydro-1-benzofuran-5-yl]isoindoline, or [9] (R)-5,6-dimethoxy-2-[2,2,4,6,7-pentamethyl-3-(4-methylphenyl)-2,3-dihydro-1-benzofuran-5-yl]isoindoline hydrochloride;

(8) The agent according to (1), which comprises (R)-(+)-5,6-dimethoxy-2-[2,2,4,6,7-pentamethyl-3-(4-methylphenyl)-2,3-dihydro-1-benzofuran-5-yl]isoindoline, (R)-(+)-5,6-dimethoxy-2-[2,2,4,6,7-pentamethyl-3-(4-(1-methylethyl)phenyl)-2,3-dihydro-1-benzofuran-5-yl]isoindoline, (R)-(+)-5,6-dimethoxy-2-[2,2,4,6,7-pentamethyl-3-(4-bromophenyl)-2,3-dihydro-1-benzofuran-5-yl]isoindoline, or a salt thereof;

(9) The agent according to (1), which comprises (i) N-(4-fluorobenzyl)-2,2,4,6,7-pentamethyl-3-phenyl-2,3-dihydro-1-benzofuran-5-amine, (ii) N-benzyl-3-(4-isopropylphenyl)-2,2,4,6,7-pentamethyl-2,3-dihydro-1-benzofuran-5-amine, (iii) 3-(4-isopropylphenyl)-N-(4-methoxybenzyl)-N,2,2,4,6,7-hexamethyl-2,3-dihydro-1-benzofuran-5-amine, (iv) 3-(4-isopropylphenyl)-N-[2-(4-methoxyphenyl)ethyl]-2,2,4,6,7-pentamethyl-2,3-dihydro-1-benzofuran-5-amine, (v) N-(4-fluorobenzyl)-3-(4-isopropylphenyl)-2,2,4,6,7-pentamethyl-2,3-dihydro-1-benzofuran-5-amine, (vi) N-(1,3-benzodioxol-5-ylmethyl)-3-(4-isopropylphenyl)-2,2,4,6,7-pentamethyl-2,3-dihydro-1-benzofuran-5-amine, (vii) N-(4-fluorobenzyl)-3-(4-fluorophenyl)-2,2,4,6,7-pentamethyl-2,3-dihydro-1-benzofuran-5-amine, (viii) N-(4-methoxybenzyl)-2,2,4,6,7-pentamethyl-3-(4-methylphenyl)-2,3-dihydro-1-benzofuran-5-amine, (ix) N-(4-fluorobenzyl)-2,2,4,6,7-pentamethyl-3-(4-methylphenyl)-2,3-dihydro-1-benzofuran-5-amine, (x) 3-(4-isopropylphenyl)-N-(4-methoxybenzyl)-2,4,6,7-tetramethyl-1-benzofuran-5-amine, (xi) N-(4-fluorobenzyl)-3-(4-isopropylphenyl)-2,4,6,7-tetramethyl-1-benzofuran-5-amine, (xii) N-(4-fluorobenzyl)-3-(4-fluorophenyl)-2,4,6,7-tetramethyl-1-benzofuran-5-amine, (xiii) N-(4-fluorobenzyl)-3-(4-isopropylphenyl)-1',4,6,7-tetramethylspiro[benzofuran-2(3H), 4'-piperidine]-5-amine or (xiv) (R)-N-(4-fluorobenzyl)-3-(4-isopropylphenyl)-2,2,4,6,7-pentamethyl-2,3-dihydro-1-benzofuran-5-amine hydrochloride;

(10) The agent according to (1), which comprises 3-(4-isopropylphenyl)-5-(4-methoxybenzyloxy)-2,2,4,6,7-pentamethyl-2,3-dihydrobenzofuran, 3-(4-methylphenyl)-2,4,6,7-tetramethylbenzofuran-5-yl 4-methoxybenzoate, 3-(4-isopropylphenyl)-2,4,6,7-tetramethylbenzofuran-5-yl 4-methoxybenzoate, 3-(4-isopropylphenyl)-5-(4-methoxybenzyloxy)-2,4,6,7-tetramethylbenzofuran, 3-(4-isopropylphenyl)-5-(4-methoxybenzyloxy)-1',4,6,7-tetramethylspiro[benzofuran-2(3H), 4'-piperidine], or a salt thereof;

(11) The agent according to (1), which is an agent for preventing or treating depression, anxiety, manic-depressive psychosis or PTSD;

(12) An agent for preventing or treating Parkinson's disease, Alzheimer's disease, amyotrophic lateral sclerosis or Huntington's disease, which comprises a protein kinase B (PKB) activating agent;

(13) The agent according to (12), wherein the PKB activating agent is the protein kinase B (PKB) activating agent according to (1);

(14) An agent for preventing or treating depression, anxiety, manic-depressive psychosis or PTSD, which comprises a PKB activating agent;

(15) An agent for preventing or treating depression, anxiety, manic-depressive psychosis or PTSD, which comprises a nerve regeneration promoting agent and/or a stem cell and/or a nerve precursor cell proliferation or differentiation promoting agent based on PKB activation;

(16) An agent for preventing or treating Parkinson's disease, Alzheimer's disease, amyotrophic lateral sclerosis or Huntington's disease, which comprises a nerve regeneration promoting agent and/or a stem cell and/or a nerve precursor cell proliferation or differentiation promoting agent based on PKB activation;

(17) Use of a PKB activating agent for preventing or treating Parkinson's disease, Alzheimer's disease, amyotrophic lateral sclerosis or Huntington's disease;

(18) Use of a PKB activating agent for preparing a medicament for preventing or treating Parkinson's disease, Alzheimer's disease, amyotrophic lateral sclerosis or Huntington's disease;

(19) A method for preventing or treating Parkinson's disease, Alzheimer's disease, amyotrophic lateral sclerosis or Huntington's disease in a mammal, which comprises administering a PKB activating agent to a mammal;

(20) Use of a PKB activating agent for preventing or treating depression, anxiety, manic-depressive psychosis or PTSD;

(21) Use of the PKB activating agent according to (1) for preparing a medicament for preventing or treating depression, anxiety, manic-depressive psychosis or PTSD;

(22) A method for preventing or treating depression, anxiety, manic-depressive psychosis or PTSD in a mammal, which comprises administering a PKB activating agent to a mammal; and

(23) A method for preventing or treating depression, anxiety, manic-depressive psychosis or PTSD in a mammal, which comprises administering the PKB activating agent according to (1) to a mammal.

DETAILED DESCRIPTION OF THE INVENTION

Figure 1:
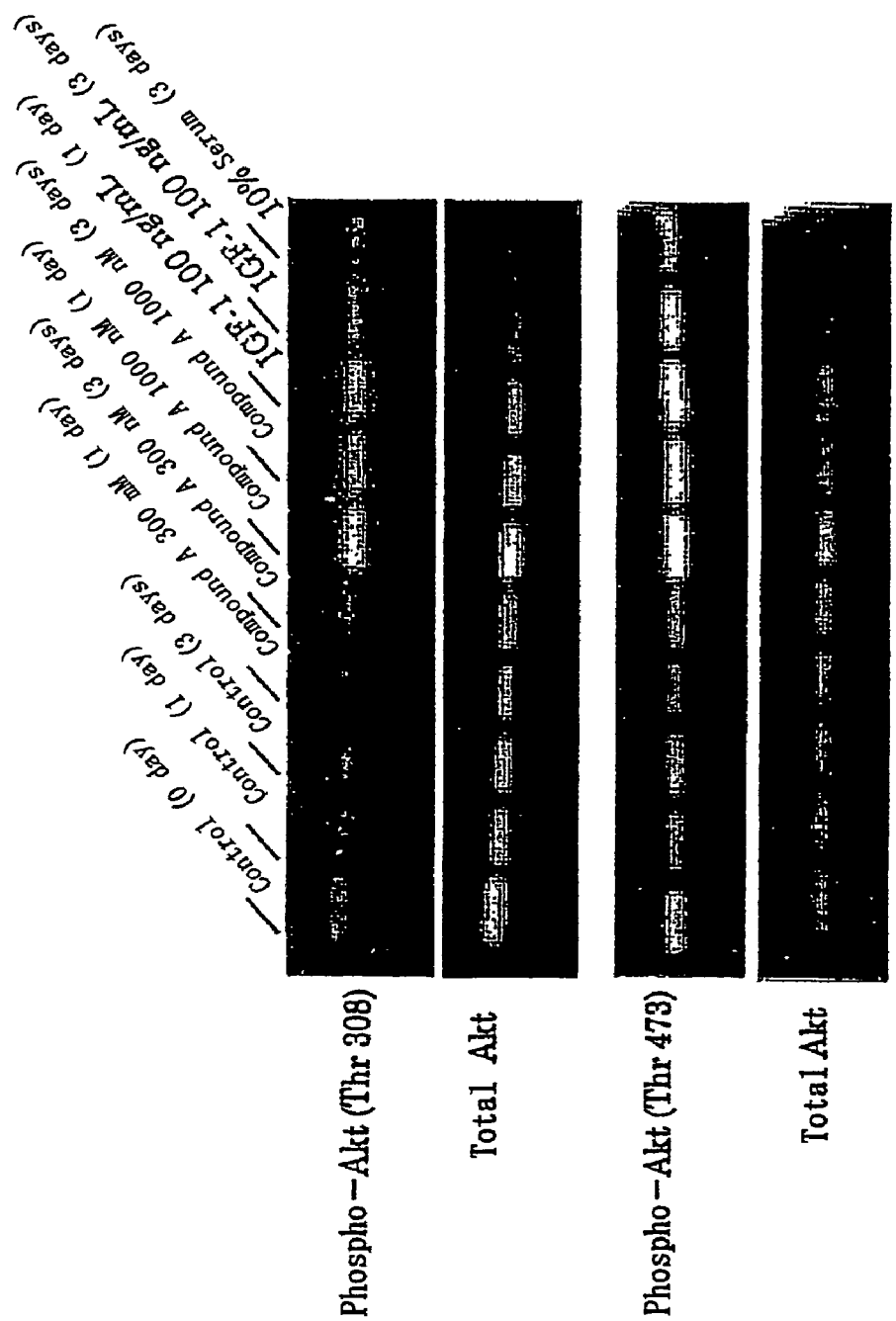
FIG. 1 is a graph showing Akt phosphorylation promoting activity of Compound A and IGF-I in a rat hippocampus glia mixed culturing system.

In the above formula (I), $\stackrel{===}{\phantom{xx}}$ represents a single bond or a double bond $\stackrel{===}{\phantom{xx}}$ is preferably a single bond.

In the above formula (I), $R^1$ and $R^2$ are the same or different, and represent a hydrogen atom, an optionally substituted hydrocarbon group, or an optionally substituted heterocyclic group, or $R^1$ and $R^2$ may be taken together with an adjacent carbon to form an optionally substituted 3- to 8-membered homocycle or heterocycle.

In the above formula, when $\stackrel{===}{\phantom{xx}}$ represents a double bond, $R^2$ is not present. That is, in the above formula, (i) when $\stackrel{===}{\phantom{xx}}$ represents a single bond, a partial structure:

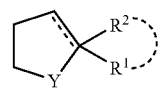

or (ii) when $\stackrel{===}{\phantom{xx}}$ represents a double bond, a partial structure:

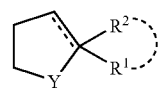

represents:

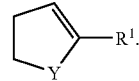

However, herein, for convenience, (i) and (ii) as a whole is represented by the formula:

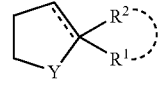

in some cases.

Examples of the "hydrocarbon group" in the "optionally substituted hydrocarbon group" represented by $R^1$ or $R^2$ include linear or cyclic hydrocarbon groups (e.g. alkyl, alkenyl, alkynyl, cycloalkyl, aryl, etc.). Among them, linear or cyclic hydrocarbon groups having 1 to 16 carbon atoms are preferable.

As the "alkyl", for example, $C_{1-6}$ alkyl (e.g. methyl, ethyl, propyl, isopropyl, butyl, isobutyl, sec-butyl, tert-butyl, pentyl, hexyl, etc.) is preferable.

As the "alkenyl", for example, $C_{2-6}$ alkenyl (e.g. vinyl, allyl, isopropenyl, butenyl, isobutenyl, sec-butenyl, etc.) is preferable.

As the "alkynyl", for example, $C_{2-6}$ alkynyl (e.g. ethynyl, propargyl, butynyl, 1-hexynyl, etc.) is preferable.

As the "cycloalkyl", for example, $C_{3-6}$ cycloalkyl (e.g. cyclopropyl, cyclobutyl, cyclopentyl, cyclohexyl, etc.) is preferable.

As the "aryl", for example, $C_{6-14}$ aryl (e.g. phenyl, 1-naphthyl, 2-naphthyl, biphenylyl, 2-anthryl, etc.) is preferable.

Examples of the "substituent" in the "optionally substituted hydrocarbon group" represented by $R^1$ or $R^2$ include (1) a halogen atom (e.g. fluorine, chlorine, bromine, iodine, etc.), (2) $C_{1-3}$ alkylenedioxy (e.g. methylenedioxy, ethylenedioxy, etc.), (3) nitro, (4) cyano, (5) optionally halogenated $C_{1-6}$ alkyl, (6) optionally halogenated $C_{2-6}$ alkenyl, (7) optionally halogenated $C_{2-6}$ alkynyl, (8) optionally halogenated $C_{3-6}$ cycloalkyl (9) $C_{6-14}$ aryl (e.g. phenyl, 1-naphthyl, 2-naphthyl, biphenylyl, 2-anthryl, etc.), (10) optionally halogenated $C_{1-6}$ alkoxy, (11) optionally halogenated $C_{1-6}$ alkylthio or mercapto, (12) hydroxy, (13) amino, (14) mono-$C_{1-6}$ alkylamino (e.g. methylamino, ethylamino, etc.), (15) mono-$C_{6-14}$ arylamino (e.g. phenylamino, 1-naphthylamino, 2-naphthylamino, etc.), (16) di-$C_{1-6}$ alkylamino (e.g. dimethylamino, diethylamino, etc.), (17) di-$C_{6-14}$ arylamino (e.g. diphenylamino, etc.), (18) acyl, (19) acylamino, (20) acyloxy, (21) optionally substituted 5- to 7-membered saturated cyclic amino, (22) 5- to 10-membered aromatic heterocyclic group (e.g. 2- or 3-thienyl, 2-, 3- or 4-pyridiyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, etc.), (23) sulfo, (24) $C_{6-14}$ aryloxy (e.g. phenyloxy, naphthyloxy, etc.), and the like.

The "hydrocarbon group" may be substituted with 1 to 5, preferably 1 to 3 the above substituents at replaceable positions and, when the number of substituents is 2 or more, respective substituents may be the same or different.

Examples of the above "optionally halogenated $C_{1-6}$ alkyl" include $C_{1-6}$ alkyl (e.g. methyl, ethyl, propyl, isopropyl, butyl, isobutyl, sec-butyl, tert-butyl, pentyl, hexyl, etc.) optionally having 1 to 5 preferably 1 to 3 halogen atoms (e.g. fluorine, chlorine, bromine, iodine, etc.). Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, and the like.

Examples of the above "optionally halogenated $C_{2-6}$ alkenyl" include $C_{2-6}$ alkenyl (e.g. vinyl, allyl, isopropenyl, butenyl, isobutenyl, sec-butenyl, etc.) optionally having 1 to 5, preferably 1 to 3 halogen atoms (e.g. fluorine, chlorine, bromine, iodine, etc.). Specific examples include vinyl, allyl, isopropenyl, butenyl, isobutenyl, sec-butenyl, 3,3,3-trifluoro-1-propenyl, 4,4,4-trifluoro-1-butenyl, and the like.

Examples of the above "optionally halogenated $C_{2-6}$ alkynyl" include $C_{2-6}$ alkynyl (e.g. ethynyl, propargyl, butynyl, 1-hexynyl, etc.) optionally having 1 to 5, preferably 1 to 3 halogen atoms (e.g. fluorine, chlorine, bromine, iodide, etc.). Specific examples include ethynyl, propargyl, butynyl, 1-hexynyl, 3,3,3-trifluoro-1-propynyl, 4,4,4-trifluoro-1-butynyl, and the like.

Examples of the above "optionally halogenated $C_{3-6}$ cycloalkyl" include $C_{3-6}$ cycloalkyl (e.g. cyclopropyl, cyclobutyl, cyclopentyl, cyclohexyl, etc.) optionally having 1 to 5, preferably 1 to 3 halogen atoms (e.g. fluorine, chlorine, bromine, iodide, etc.). Specific examples include cyclopropyl, cyclobutyl, cyclopentyl, cyclohexyl, 4,4-dichlorocyclohexyl, 2,2,3,3-tetrafluorocyclopentyl, 4-chlorocyclohexyl, and the like.

Examples of the above "optionally halogenated $C_{1-6}$ alkoxy" include $C_{1-6}$ alkoxy (e.g. methoxy, ethoxy, propoxy, isopropoxy, butoxy, isobutoxy, sec-butoxy, pentyloxy, hexyloxy, etc.) optionally having 1 to 5, preferably 1 to 3 halogen atoms (e.g. fluorine, chlorine, bromine, iodine, etc.). Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, and the like.

Examples of the above "optionally halogenated $C_{1-6}$ alkylthio" include $C_{1-6}$ alkylthio (e.g. methylthio, ethylthio, propylthio, isopropylthio, butylthio, sec-butylthio, tert-butylthio, etc.) optionally having 1 to 5, preferably 1 to 3 halogen atoms (e.g. fluorine, chlorine, bromine, iodine, etc.). Specific examples include methylthio, difluoromethylthio, trifluoromethylthio, ethylthio, propylthio, isopropylthio, butylthio, 4,4,4-trifluorobutylthio, pentylthio, hexylthio, and the like.

Examples of the above "acyl" include formyl, carboxy, carbamoyl, $C_{1-6}$ alkyl-carbonyl (e.g. acetyl, propionyl, etc.), $C_{3-6}$ cycloalkyl-carbonyl (e.g. cyclopropylcarbonyl, cyclopentylcarbonyl, cyclohexylcarbonyl, etc.), $C_{1-6}$ alkoxy-carbonyl (e.g. methoxycarbonyl, ethoxycarbonyl, propoxycarbonyl, tert-butoxycarbonyl, etc.), $C_{6-14}$ aryl-carbonyl (e.g. benzoyl, 1-naphthoyl, 2-naphthoyl, etc.), $C_{7-16}$ aralkyl-carbonyl (e.g. phenylacetyl, phenylpropionyl, etc.), $C_{6-14}$ aryloxy-carbonyl (e.g. phenoxycarbonyl, etc.), $C_{7-16}$ aralkyloxycarbonyl (e.g. benzyloxycarbonyl, phenethyloxycarbonyl, etc.), 5- or 6-membered heterocyclic carbonyl (e.g. nicotinoyl, isonicotinoyl, 2-thenoyl, 3-thenoyl, 2-furoyl, 3-furoyl, morpholinocarbonyl, thiomorpholinocarbonyl, piperidinocarbonyl, 1-pyrrolidinylcarbonyl, etc.), mono-$C_{1-6}$ alkylcarbamoyl (e.g. methylcarbamoyl, ethylcarbamoyl, etc.), di-$C_{1-6}$ alkyl-carbamoyl (e.g. dimethylcarbamoyl, diethylcarbamoyl, ethylmethylcarbamoyl, etc.), $C_{6-14}$ aryl-carbamoyl (e.g. phenylcarbamoyl, 1-naphthylcarbamoyl, 2-naphthylcarbamoyl, etc.), thiocarbamoyl, 5- or 6-membered heterocyclic carbamoyl (e.g. 2-pyridylcarbamoyl, 3-pyridylcarbamoyl, 4-pyridylcarbamoyl, 2-thienylcarbamoyl, 3-thienylcarbamoyl, etc.), $C_{1-6}$ alkylsulfonyl (e.g. methylsulfonyl, ethylsulfonyl, etc.), $C_{6-14}$ arylsulfonyl (e.g. phenylsulfonyl, 1-naphthylsulfonyl, 2-naphthylsulfonyl, etc.), $C_{1-6}$ alkylsulfinyl (e.g. methylsulfinyl, ethylsulfinyl, etc.), $C_{6-14}$ arylsulfinyl (e.g. phenylsulfinyl, 1-naphthylsulfinyl, 2-naphthylsulfinyl, etc.), and the like.

Examples of the above "acylamino" include formylamino, $C_{1-6}$ alkyl-carbonylamino (e.g. acetylamino, etc.), $C_{6-14}$ arylcarbonylamino (e.g. phenylcarbonylamino, naphthylcarbonylamino, etc.), $C_{1-6}$ alkoxy-carbonylamino (e.g. methoxycarbonylamino, ethoxycarbonylamino, propoxycarbonylamino, butoxycarbonylamino. etc.), $C_{1-6}$ alkylsulfonylamino (e.g. methylsulfonylamino, ethylsulfonylamino, etc.), $C_{6-14}$ arylsulfonylamino (e.g. phenylsulfonylamino, 2-naphthylsulfonylamino, 1-naphthylsulfonylamino, etc.), and the like.

Examples of the above "acyloxy" include $C_{1-6}$ alkyl-carbonyloxy (e.g. acetoxy, propionyloxy, etc.), $C_{6-14}$ arylcarbonyloxy (e.g. benzoyloxy, naphthylcarbonyloxy, etc.), $C_{1-6}$ alkoxy-carbonyloxy (e.g. methoxycarbonyloxy, ethoxycarbonyloxy, propoxycarbonyloxy, butoxycarbonyloxy, etc.), mono-$C_{1-6}$ alkyl-carbamoyloxy (e.g. methylcarbamoyloxy, ethylcarbamoyloxy, etc.), di-$C_{1-6}$ alkyl-carbamoyloxy (e.g. dimethylcarbamoyloxy, diethylcarbamoyloxy, etc.), $C_{6-14}$ aryl-carbamoyloxy (e.g. phenylcarbamoyloxy, naphthylcarbamoyloxy etc.), nicotinoyloxy, and the like.

Examples of the above "5- to 7-membered saturated cyclic amino" of the "optionally substituted 5- to 7-membered saturated cyclic amino" include morpholino, thiomorpholino, piperazin-1-yl, piperidino, pyrrolidin-1-yl, and the like. Examples of the "substituent" of the "optionally substituted 5- to 7-membered saturated cyclic amino" include 1 to 3 of $C_{1-6}$ alkyl (e.g. methyl, ethyl, propyl, isopropyl, butyl, isobutyl, sec-butyl, tert-butyl, pentyl, hexyl, etc.), $C_{6-14}$ aryl (e.g. phenyl, 1-naphthyl, 2-naphthyl, biphenylyl, 2-anthryl, etc.), 5- to 10-membered aromatic heterocyclic group (e.g. 2- or 3-thienyl, 2-, 3- or 4-pyridyl, 2-, 3-, 4-, 5- or 8-quinolyl, 1-, 3-, 4- or 5-isoqiunolyl, 1-, 2- or 3-indolyl, 2-benzothiazolyl, 2-benzo[b]thienyl, benzo[b]furanyl, etc.), and the like.

Examples of the "heterocyclic group" of the "optionally substituted heterocyclic group" represented by $R^1$ or $R^2$ include 5- to 14-membered heterocyclic groups (aromatic heterocyclic group, saturated or unsaturated non-aromatic heterocyclic group) containing 1 to 4 hetero atoms selected from a nitrogen atom, a sulfur atom and an oxygen atom in addition to carbon atoms.

Examples of the "aromatic heterocyclic group" include 5- to 14-membered, preferably 5- to 10-membered aromatic heterocyclic groups containing 1 or more (e.g. 1 to 4) hetero atoms selected from a nitrogen atom, a sulfur atom and an oxygen atom in addition to carbon atoms. Specific examples include aromatic heterocycles such as thiophene, benzothiophene, benzofuran, benzimidazole, benzoxazole, benzothiazole, benzisothiazole, naphtho[2,3-b]thiophene, furan, isoindolidine, xanthrene, phenoxathiin, pyrrole, imidazole, pyrazole, pyridine, pyrazine, pirimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, oxazole, isoxazole, phlazane, phenoxazine, and the like; and monovalent groups obtained by removing any one hydrogen atom from fused rings of these rings (preferably monocycles) with 1 or more (preferably 1 or 2) aromatic rings (e.g. benzene ring etc.); and the like.

Preferable examples of the "aromatic heterocyclic group" include 5- or 6-membered aromatic heterocyclic groups which may be fused with one benzene ring, and the like. Specific examples include 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, 2- or 3-thienyl, and the like. More preferred are 2- or 3-thienyl, 2-, 3- or 4-pyridyl, 2- or 3-quinolyl, 1-isoquinolyl, 1- or 2-indolyl, 2-benzothiazolyl, and the like.

Examples of the "non-aromatic heterocyclic group" include 3- to 8-membered (preferably 5- to 6-membered) saturated or unsaturated (preferably saturated) non-aromatic heterocyclic groups (aliphatic heterocyclic groups) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, and the like.

As the "substituent" of the "optionally substituted heterocyclic group" represented by $R^1$ or $R^2$, the same number of the same substituents as those of the above "optionally substituted hydrocarbon group" represented by $R^1$ or $R^2$ are used.

Examples of the "3- to 8-membered homocycle" of the "optionally substituted 3- to 8-membered homocycle" formed by $R^1$ and $R^2$ include $C_{3-8}$ cycloalkane such as cyclopropane, cyclobutane, cyclopentane, cyclehexane, and the like.

Examples of the "3- to 8-membered heterocycle" of the "optionally substituted 3- to 8-membered heterocycle" formed by $R^1$ and $R^2$ include 3- to 8-membered heterocycles containing 1 to 4 hetero atoms selected from a nitrogen atom, a sulfur atom and an oxygen atom in addition to carbon atoms, such as aziridine, azetidine, morpholine, thiomorpholine, piperazine, piperidine, pyrrolidine, hexamethyleneimine, heptamethyleneimine, hexahydropyrimidine, and the like.

As the "substituent" in the "optionally substituted 3- to 8-membered homocycle or heterocycle" formed by $R^1$ and $R^2$, the same number of the same substituents as those of the above "optionally substituted hydrocarbon group" represented by $R^1$ or $R^2$ are used.

As the "optionally substituted hydrocarbon group" and the "optionally substituted heterocyclic group" represented by $R^3$, the same "optionally substituted hydrocarbon group" and "optionally substituted heterocyclic group" as those represented by the above $R^1$ or $R^2$ are used.

In the above formula, W represents:
(i) a group represented by the formula:

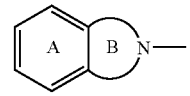

(Wa)

wherein the A ring represents an optionally substituted benzene ring, and the B ring represents an optionally substituted 5- to 7-membered nitrogen-containing heterocycle, (ii) a group represented by the formula:

(Wb)

wherein $R^4$ represents (1) an aliphatic hydrocarbon group substituted with an optionally substituted aromatic group, and optionally further substituted, or (2) an acyl group containing an optionally substituted aromatic group, and $R^5$ represents a hydrogen atom, $C_{1-6}$ alkyl or an acyl group], or (iii) a group represented by the formula:

$$R^{4c}-X-$$ (Wc)

wherein $R^{4c}$ represents an optionally substituted aromatic group, an optionally substituted aliphatic hydrocarbon group, or acyl, and X represents an oxygen atom or an optionally oxidized sulfur atom.

When W is Wa, in the above formula, $R^3$ is preferably a hydrogen atom, an optionally substituted hydrocarbon group, or an optionally substituted heterocyclic group (hereinafter, referred to as $R^{3a}$ in some cases).

In the above formula, the A ring represents an optionally substituted benzene ring.

As the "substituent" in the "optionally substituted benzene ring" represented by the A ring, the benzene ring may have the same 1 to 4 (preferably 1 or 2) substituents as those of the above "optionally substituted hydrocarbon group" represented by $R^1$ or $R^2$ at replaceable positions. When the number of substituents is 2 or more, respective substituents may be the same or different.

In the above formula, the B ring represents an optionally substituted 5- to 7-membered nitrogen-containing heterocycle.

Examples of the "5- to 7-membered nitrogen-containing heterocycle" represented by the B ring include 5- to 7-membered nitrogen-containing heterocycles such as pyrrole (e.g.

1H-pyrrole, etc.), dihydropyrrole (e.g. 2,5-dihydro-1H-pyrrole, etc.), dihydropyridine (e.g. 1,2-dihydropyrridine, etc.), tetrahydropyridine (e.g. 1,2,3,4-tetrahydropyrridine, etc.), azepine (e.g. 1H-azepine, etc.), dihydroazepine (e.g. 2,3-dihydro-1H-azepine, 2,5-dihydro-1H-azepine, 2,7-dihydro-1H-azepine, etc.), tetrahydroazepine (e.g. 2,3,6,7-tetrahydro-1H-azepine, 2,3,4,7-tetrahydro-1H-azepine, etc.), and the like.

As the "substituent" in the "optionally substituted 5- to 7-membered nitrogen-containing heterocycle" represented by the B ring, the same number of the same substituents as those of the above "optionally substituted hydrocarbon group" represented by $R^1$ or $R^2$ may be used. As the substituent of the B ring, an oxo group may also be used.

Specific examples of the group represented by the formula:

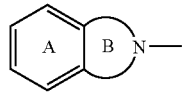

wherein respective symbols are as defined above, include groups represented by the formulas:

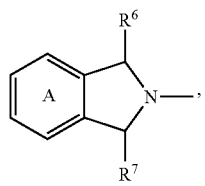 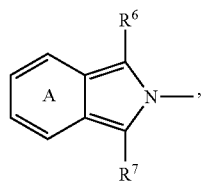

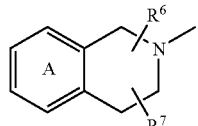 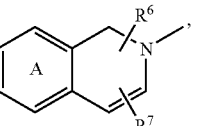

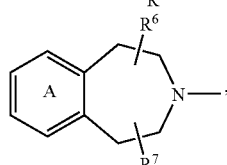 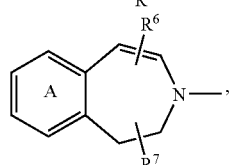

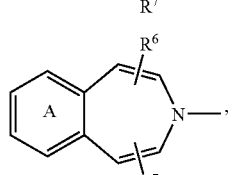 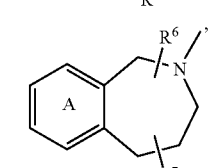

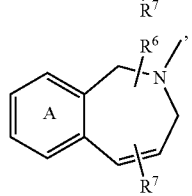 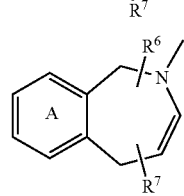

wherein $R^6$ and $R^7$ are the same or different, and represent a hydrogen atom, halogen or an optionally substituted hydrocarbon group, and an A ring is as defined above, preferably groups represented by the formulas:

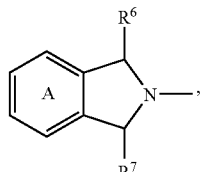 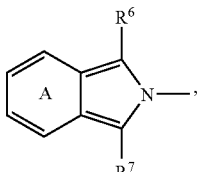

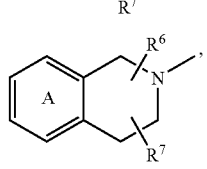 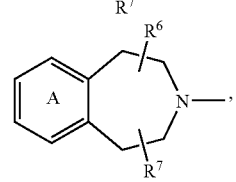

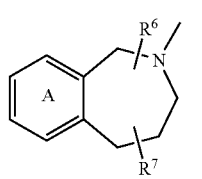

wherein respective symbols are as defined above, more preferably groups represented by the formulas:

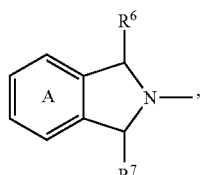 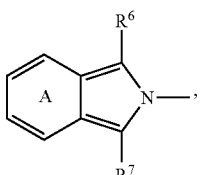

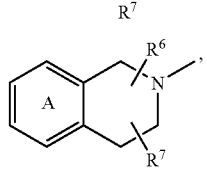 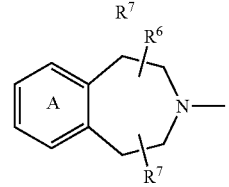

wherein respective symbols are as defined above, inter alia, particularly preferably groups represented by the formulas:

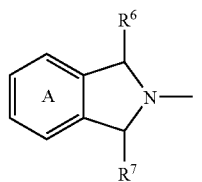 and 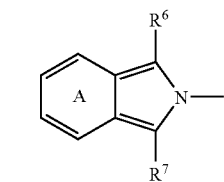

wherein respective symbols are as defined above.

As the "halogen" or the "optionally substituted hydrocarbon group" represented by $R^6$ and $R^7$, the same "halogen" or "optionally substituted hydrocarbon group" as those of the "substituent" of the above B ring are used.

In the above formula, the C ring represents a benzene ring optionally further substituted in addition to a group represented by the formula W.

The C ring may have 1 to 3 (preferably 1) groups represented by the formula W at replaceable positions and, when the number of substituents is 2 or more, respective substituents may be the same or different.

Examples of the "substituent" which may be further possessed by the C ring include the same substituents as those of the above "optionally substituted hydrocarbon group" represented by $R^1$ or $R^2$. In addition, the "$C_{1-6}$ alkyl" as the "substituent" of the C ring may be substituted with "4- to 8-membered lactone optionally substituted with hydroxy (e.g. 3-hydroxy-δ-valerolactone, etc.)", or the like. The C ring may have 1 to 3 (preferably 3) of these substituents at replaceable positions and, when the number of substituents is 2 or more, respective substituents may be the same or different.

As the C ring, a benzene ring substituted with 3 $C_{1-6}$ alkyls such as methyl is preferable.

When W is Wa, as the C ring in the above formula, a benzene ring optionally further substituted with substituent(s) selected from halogen, optionally halogenated lower alkyl, optionally halogenated lower alkoxy and optionally halogenated lower alkylthio in addition to the group represented by the formula:

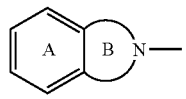

wherein respective symbols are as defined above (hereinafter, referred to as $C^1$ ring in some cases), is preferable.

The $C^1$ ring may have 1 to 3 (preferably 1) of substituents represented by the formula:

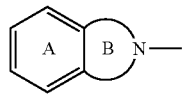

at replaceable positions and, when the number of substituents is 2 or more, respective substituents may be the same or different.

Examples of the "halogen" as the "substituent" which may be further possessed by the $C^1$ ring include fluorine, chlorine, bromine, iodine, and the like. Examples of the "optionally halogenated lower alkyl" include $C_{1-6}$ alkyl (e.g. methyl, ethyl, propyl, isopropyl, butyl, isobutyl, sec-butyl, tert-butyl, pentyl, hexyl, etc.) optionally having 1 to 5, preferably 1 to 3 halogen atoms (e.g. fluorine, chlorine, bromine, iodine, etc.), and specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, and the like. Examples of the "optionally halogenated lower alkoxy" include $C_{1-6}$ alkoxy (e.g. methoxy, ethoxy, propoxy, isopropoxy, butoxy, isobutoxy, sec-butoxy, pentyloxy, hexyloxy, etc.) optionally having 1 to 5, preferably 1 to 3 halogen atoms (e.g. fluorine, chlorine, bromine, iodine, etc.). Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, and the like. Examples of the "optionally halogenated lower alkylthio" include $C_{1-6}$ alkylthio (e.g. methylthio, ethylthio, propylthio, isopropylthio, butylthio, sec-butylthio, tert-butylthio, etc.) optionally having 1 to 5, preferably 1 to 3 halogen atoms (e.g. fluorine, chlorine, bromine, iodine, etc.). Specific examples include methylthio, difluoromethylthio, trifluoromethylthio, ethylthio, propylthio, isopropylthio, butylthio, 4,4,4-trifluorobutylthio, pentylthio, hexylthio, and the like.

The $C^1$ ring may have 1 to 3 (preferably 3) of these substituents at replaceable positions and, when the number of substituents is 2 or more, respective substituents may be the same or different.

When W represents Wb, in the above formula, $R^3$ is preferably an optionally substituted $C_{6-14}$ aryl group (hereinafter, referred to as $R^{3b}$ in some cases).

Examples of the "$C_{6-14}$ aryl" of the "optionally substituted $C_{6-14}$ aryl" represented by $R^{3b}$ include $C_{6-14}$ aryl groups such as phenyl, 1-naphthyl, 2-naphthyl, biphenylyl, anthryl, and the like.

As the "substituent" of the "optionally substituted $C_{6-14}$ aryl", the same number of the same substituents as those of the above "optionally substituted hydrocarbon group" represented by $R^1$ or $R^2$ are used.

In the above formula, $R^4$ represents (1) an aliphatic hydrocarbon group substituted with an optionally substituted aromatic group, and optionally further substituted, or (2) an acyl group containing an optionally substituted aromatic group.

Examples of the "aromatic group" of the "optionally substituted aromatic group" as the substituent of the "aliphatic hydrocarbon group substituted with an optionally substituted aromatic group, and optionally further substituted" represented by $R^4$ include an aromatic hydrocarbon group, and an aromatic heterocyclic group.

Examples of the "aromatic hydrocarbon group" include monocyclic or fused polycyclic (di- or tri-cyclic) aromatic hydrocarbon groups having 6 to 14 carbon atoms. Specific examples include $C_{6-14}$ aryl such as phenyl, 1-naphthyl, 2-naphthyl, biphenylyl, anthryl, and the like, preferably $C_{6-10}$ aryl such as phenyl, 1-naphthyl, 2-naphthyl, and the like.

Examples of the "aromatic heterocyclic group" include 5- to 14-membered, preferably 5- to 10-membered aromatic heterocyclic groups containing 1 or more (e.g. 1 to 4) hetero atoms selected from a nitrogen atom, a sulfur atom and an oxygen atom in addition to carbon atoms. Specific examples include aromatic heterocycles such as thiophene, benzothiophene, benzofuran, benzimidazole, benzoxazole, benzothiazole, benzisothiazole, naphtho[2,3-b]thiophene, furan, isoindolidine, xanthrene, phenoxathiin, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, oxazole, isoxazole, phlazane, phenoxazine, and the like; and monovalent groups obtained by removing an arbitrary hydrogen atom from rings formed by fusing these rings (preferably monocycle) with 1 to plural (preferably 1 or 2) aromatic rings (e.g. benzene ring, etc.).

Preferable examples of the "aromatic heterocyclic group" include 5- or 6-membered aromatic heterocyclic groups which may be fused with one benzene ring. Specific examples include 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, 2- or 3-thienyl, and the like. Further preferred are 2- or 3-thienyl, 2-, 3- or 4-pyridyl, 2- or 3-quinolyl, 1-isoquinolyl, 1- or 2-indolyl, 2-benzothiazolyl, and the like.

As the "substituent" of the "optionally substituted aromatic group", the same number of the same substituents as those of the above "optionally substituted hydrocarbon group" represented by $R^1$ or $R^2$ are used.

Examples of the "aliphatic hydrocarbon group" of the "aliphatic hydrocarbon group substituted with an optionally substituted aromatic group, and optionally further substituted" represented by $R^4$ include alkyl, alkenyl, alkynyl, and cycloalkyl. Inter alia, $C_{1-10}$alkyl, $C_{2-10}$ alkenyl, $C_{2-10}$ alkynyl and $C_{3-10}$ cycloalkyl are preferable.

As the "alkyl", for example, $C_{1-6}$ alkyl (e.g. methyl, ethyl, propyl, isopropyl, butyl, isobutyl, sec-butyl, tert-butyl, pentyl, hexyl etc.) is preferable.

As the "alkenyl", for example, $C_{2-6}$ alkenyl (e.g. vinyl, allyl, isopropenyl, butenyl, isobutenyl, sec-butenyl etc.) is preferable.

As the "alkynyl", for example, $C_{2-6}$ alkynyl (e.g. ethynyl, propargyl, butynyl, 1-hexynyl etc.) is preferable.

As the "cycloalkyl", for example, $C_{3-6}$ cycloalkyl (e.g. cyclopropyl, cyclobutyl, cyclopentyl, cyclohexyl etc.) is preferable.

Inter alia, $C_{1-6}$ alkyl is preferable.

The "aliphatic hydrocarbon group" may be optionally substituted with 1 to 3 "optionally substituted aromatic groups" at replaceable positions, and when the number of the substituents is 2 or more, respective substituents may be the same or different.

As the "substituent" which the "aliphatic hydrocarbon group" may be optionally further substituted with, the same number of the same substituents as those of the "optionally substituted hydrocarbon group" represented by $R^1$ or $R^2$ are used.

As the "acyl group" of the "acyl group containing an optionally substituted aromatic group" represented by $R^4$, the same acyl group as that of the "substituent" of the "optionally substituted hydrocarbon group" represented by $R^1$ or $R^2$ is used.

As the "optionally substituted aromatic group" of the "acyl group containing an optionally substituted aromatic group" represented by $R^4$, the same optionally substituted aromatic group as that of the "aliphatic hydrocarbon group substituted with an optionally substituted aromatic group, and optionally further substituted" represented by $R^4$ is used.

Specific examples of the "acyl group containing an optionally substituted aromatic group" represented by $R^4$, preferably, include $C_{6-14}$ aryl-carbonyl (e.g. benzoyl, 1-naphthoyl, 2-naphthoyl etc.), $C_{7-16}$ aralkyl-carbonyl (e.g. phenylacetyl, phenylpropionyl etc.), $C_{6-14}$ aryloxy-carbonyl (e.g. phenoxycarbonyl etc.), $C_{7-16}$ aralkyloxy-carbonyl (e.g. benzyloxycarbonyl, phenethyloxycarbonyl etc.), 5- or 6-membered heterocyclic carbonyl (e.g. nicotinoyl, isonicotinoyl, 2-thenoyl, 3-thenoyl, 2-furoyl, 3-furoyl, morpholinocarbonyl, thiomorpholinocarbonyl, piperidinocarbonyl, 1-pyrrolidinylcarbonyl etc.), $C_{6-14}$ aryl-carbamoyl (e.g. phenylcarbamoyl, 1-naphthylcarbamoyl, 2-naphthylcarbamoyl etc.), 5- or 6-membered heterocyclic carbamoyl (e.g. 2-pyridylcarbamoyl, 3-pyridylcarbamoyl, 4-pyridylcarbamoyl, 2-thienylcarbamoyl, 3-thienylcarbamoyl etc.), $C_{6-14}$ arylsulfonyl (e.g. phenylsulfonyl, 1-naphthylsulfonyl, 2-naphthylsulfonyl etc.), and $C_{6-14}$ arylsulfinyl (e.g. phenylsulfinyl, 1-naphthylsulfinyl, 2-naphthylsulfinyl etc.).

In the above formula, $R^5$ represents a hydrogen atom, a $C_{1-6}$ alkyl group or an acyl group.

Examples of a $C_{1-6}$ alkyl group represented by $R^5$ include methyl, ethyl, propyl, isopropyl, butyl, isobutyl, sec-butyl, tert-butyl, pentyl and hexyl.

As the "acyl group" represented by $R^5$, the same acyl group as that of the "substituent" of the "optionally substituted hydrocarbon group" represented by $R^1$ or $R^2$ is used.

When W is Wb, in the above formula, the C ring represents a benzene ring which may be further substituted in addition to a group represented by the formula —$NR^4(R^5)$ (hereinafter, referred as the $C^2$ ring in some cases).

The $C^2$ ring may be substituted with 1 to 3 groups represented by the formula —$NR^4(R^5)$ at replaceable positions and, when the number of the substituents is 2 or more, respective substituents may be the same or different.

Examples of the "substituent" with which the $C^2$ ring may be further substituted in addition to a group represented by the formula —$NR^4(R^5)$ include a halogen atom (e.g. fluorine, chlorine, bromine, iodine etc.), $C_{1-3}$ alkylenedioxy (e.g. methylenedioxy, ethylenedioxy etc.), nitro, cyano, optionally halogenated $C_{1-6}$ alkyl, optionally halogenated $C_{2-6}$ alkenyl, optionally halogenated $C_{2-6}$ alkynyl, optionally halogenated $C_{3-6}$ cycloalkyl, $C_{6-14}$ aryl (e.g. phenyl, 1-naphthyl, 2-naphthyl, biphenylyl, 2-anthryl etc.), optionally halogenated $C_{1-6}$ alkoxy, hydroxy, amino, mono-$C_{1-6}$ alkylamino (e.g. methylamino, ethylamino etc.), mono-$C_{6-14}$ arylamino (e.g. phenylamino, 1-naphthylamino, 2-naphthylamino etc.), di-$C_{1-6}$ alkylamino (e.g. dimethylamino, diethylamino etc.), di-$C_{6-14}$ arylamino (e.g. diphenylamino etc.), acyl, acylamino, optionally substituted 5- to 7-membered saturated cyclic amino, 5- to 10-membered aromatic heterocyclic groups (e.g. 2- or 3-thienyl, 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl etc.) and sulfo.

Examples of the "optionally halogenated $C_{1-6}$ alkyl", the "optionally halogenated $C_{2-6}$ alkenyl", the "optionally halogenated $C_{2-6}$ alkynyl", the "optionally halogenated $C_{3-6}$ cycloalkyl", the "optionally halogenated $C_{1-6}$ alkoxy", the "acyl", the "acylamino" and the "optionally substituted 5- to 7-membered saturated cyclic amino" include the same groups as those of the "substituent" of the "optionally substituted hydrocarbon group" represented by $R^1$ or $R^2$.

$R^{4c}$ represents an optionally substituted aromatic group, an optionally substituted aliphatic hydrocarbon group or an acyl group.

Examples of the "aromatic group" of the "optionally substituted aromatic group" represented by R include an aromatic hydrocarbon group and an aromatic heterocyclic group.

Examples of the "aromatic hydrocarbon group" include monocyclic or fused polycyclic (bi- or tri-cyclic) aromatic hydrocarbon groups having 6 to 14 carbon atoms. Specific examples thereof include $C_{6-14}$ aryl such as phenyl, 1-naphthyl, 2-naphthyl, biphenylyl and anthryl.

Examples of the "aromatic heterocyclic group" include 5- to 14-membered, preferably 5- to 10-membered aromatic heterocyclic groups containing 1 or more (e.g. 1 to 4) hetero atoms selected from a nitrogen atom, a sulfur atom and an oxygen atom in addition to carbon atoms. Specific examples thereof include aromatic heterocycles such as thiophene, benzothiophene, benzofuran, benzimidazole, benzoxazole, benzothiazole, benzisothiazole, naphtho[2,3-b]thiophene, furan, isoindolizine, xanthrene, phenoxathiin, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, oxazole, isoxazole, furazan and phenoxazine, and monovalent groups obtained by removing one hydrogen atom from fused rings of the above-mentioned rings (preferably monocycles) with 1 or more (preferably 1 or 2) aromatic rings (e.g. benzene ring etc.).

Preferable examples of the "aromatic heterocyclic group" include 5- or 6-membered aromatic heterocyclic groups which may be fused with one benzene ring. Specific examples thereof include 2-, 3- or 4-pyridyl, 2-, 3-, 4-, 5- or 8-quinolyl, 1-, 3-, 4- or 5-isoquinolyl, 1-, 2- or 3-indolyl, 2-benzothiazolyl, 2-benzo[b]thienyl, benzo[b]furanyl, and 2- or 3-thienyl. Further preferable examples include 2- or 3-thienyl, 2-, 3- or 4-pyridyl, 2- or 3-quinolyl, 1-isoquinolyl, 1- or 2-indolyl, and 2-benzothiazolyl.

Examples of the "substituent" of the "optionally substituted aromatic group" include a halogen atom (e.g. fluorine, chlorine, bromine, iodine etc.), $C_{1-3}$ alkylenedioxy (e.g. methylenedioxy, ethylenedioxy etc.), nitro, cyano, optionally halogenated $C_{1-6}$ alkyl, optionally halogenated $C_{2-6}$ alkenyl, optionally halogenated $C_{2-6}$ alkynyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g. methylamino, ethylamino, propylamino, isopropylamino, butylamino etc.), di-$C_{1-6}$ alkylamino (e.g. dimethylamino, diethylamino, dipropylamino, dibutylamino, ethylmethylamino etc.), optionally substituted 5- to 7-membered saturated cyclic amino, acyl, acylamino, acyloxy, sulfo, $C_{6-14}$ aryl (e.g. phenyl, 1-naphthyl, 2-naphthyl etc.), and $C_{6-14}$ aryloxy (e.g. phenyloxy, naphthyloxy etc.).

Examples of the "optionally halogenated $C_{1-6}$ alkyl", the "optionally halogenated $C_{2-6}$ alkenyl", the "optionally halogenated $C_{2-6}$ alkynyl", the "optionally halogenated $C_{3-6}$ cycloalkyl", the "optionally halogenated $C_{1-6}$ alkoxy", the "optionally halogenated $C_{1-6}$ alkylthio", the "optionally substituted 5- to 7-membered saturated cyclic amino", the "acyl", the "acylamino" and the "acyloxy" include the same groups as those of the "substituent" of the "optionally substituted hydrocarbon group" represented by $R^1$ or $R^2$.

The "aromatic group" may be optionally substituted with 1 to 3 above-mentioned substituents at replaceable positions and, when the number of the substituents is 2 or more, respective substituents may be the same or different.

Preferable examples of the "optionally substituted aromatic group" include phenyl, 2-, 3- or 4-pyridyl, 2- or 3-quinolyl, and 1-isoquinolyl, each of which may be optionally substituted with 1 to 3 substituents selected from halogen, $C_{1-3}$ alkylenedioxy, nitro, cyano, optionally halogenated $C_{1-6}$ alkyl, optionally halogenated $C_{2-6}$ alkenyl, optionally halogenated $C_{2-6}$ alkynyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino, di-$C_{1-6}$ alkylamino, optionally substituted 5- to 7-membered saturated cyclic amino, acyl, acylamino, acyloxy, sulfo, $C_{6-14}$ aryl and $C_{6-14}$ aryloxy.

Examples of the "aliphatic hydrocarbon group" of the "optionally substituted aliphatic hydrocarbon group" represented by $R^{4c}$ include alkyl, alkenyl, alkynyl, and cycloalkyl. Among them, $C_{1-10}$ alkyl, $C_{2-10}$ alkenyl, $C_{2-10}$ alkynyl, and $C_{3-10}$ cycloalkyl are preferable.

As the "alkyl", for example, $C_{1-6}$ alkyl (e.g. methyl, ethyl, propyl, isopropyl, butyl, isobutyl, sec-butyl, tert-butyl, pentyl, hexyl etc.) is preferable.

As the "alkenyl", for example, $C_{2-6}$ alkenyl (e.g. vinyl, allyl, isopropenyl, butenyl, isobutenyl, sec-butenyl etc.) is preferable.

As the "alkynyl", for example, $C_{2-6}$ alkynyl (e.g. ethynyl, propargyl, butynyl, 1-hexynyl etc.) is preferable.

As the "cycloalkyl", for example, $C_{3-6}$ cycloalkyl (e.g. cyclopropyl, cyclobutyl, cyclopentyl, cyclohexyl etc.) is preferable.

Inter alia, $C_{1-6}$ alkyl is preferable.

As the "substituent" which the "aliphatic hydrocarbon group" may be optionally substituted with, the same number of the same substituents as those of the "optionally substituted hydrocarbon group" represented by $R^1$ or $R^2$ are used.

Preferable examples of this "substituent" include acyl (e.g. carboxy, $C_{1-6}$ alkyl-carbonyl, $C_{1-6}$ alkoxy-carbonyl, $C_{6-14}$ aryl-carbonyl etc.).

As the "acyl group" represented by R c, for example, the same acyl group as that of the "substituent" of the "optionally substituted hydrocarbon group" represented by $R^1$ or $R^2$ is used.

Examples of the "optionally oxidized sulfur atom" represented by X or Y include S, SO and $SO_2$.

Examples of the "substituent" of the "optionally substituted imino" represented by Y include an optionally substituted hydrocarbon group and acyl.

Examples of the "optionally substituted hydrocarbon group" are the same as those of the "optionally substituted hydrocarbon group" represented by $R^1$ or $R^2$.

Examples of the "acyl" are the same as those of the "acyl" mentioned above as the "substituent" of the "optionally substituted hydrocarbon group" represented by $R^1$ or $R^2$.

Preferable examples of the "optionally substituted imino" represented by Y include imino, $C_{1-6}$ alkylimino (e.g. methylimino, ethylimino etc.), $C_{6-14}$ arylimino (e.g. phenylimino, 1-naphthylimino, 2-naphthylimino etc.), and $C_{7-16}$ aralkylimino (e.g. benzylimino).

X and Y are preferably an oxygen atom.

Thus, the compound (I) of the present invention includes a compound (Ia) represented by the formula:

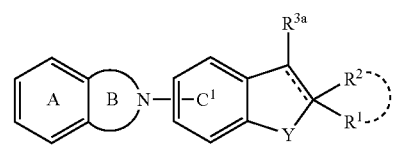

wherein respective symbols are as defined above, a compound (Ib) represented by the formula:

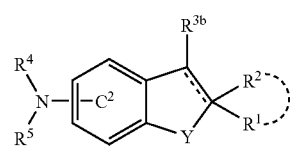

wherein respective symbols are as defined above, and a compound (Ic) represented by the formula:

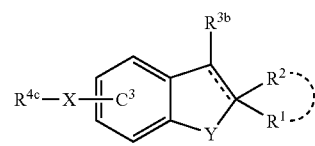

wherein respective symbols are as defined above.

In the compound (Ia), for example, $R^1$ and $R^2$ are the same or different and are preferably a hydrogen atom or an optionally substituted $C_{1-6}$ alkyl group (particularly, $C_{1-3}$ alkyl group such as methyl) or taken together with the adjacent carbon atom to form an optionally substituted 3- to 8-membered homocycle or heterocycle, more preferably $R^1$ and $R^2$ are each a $C_{1-6}$ alkyl group. When ---- represents a double bond, $R^2$ is not present and $R^1$ is preferably an optionally substituted $C_{1-6}$ alkyl group, more preferably a $C_{1-3}$ alkyl group such as methyl.

As $R^{3a}$, for example, an optionally substituted $C_{6-14}$ aryl group is preferable.

As the A ring, for example, a benzene ring optionally substituted with 1 to 3 substituents selected from halogen, $C_{1-6}$ alkyl, $C_{1-6}$ alkoxy and $C_{1-6}$ alkylenedioxy is preferable.

As the B ring, for example, a 5- to 7 membered nitrogen-containing heterocycle optionally substituted with 1 to 2 $C_{1-6}$ alkyl is preferable.

As the $C^1$ ring, a benzene ring optionally further substituted with 1 to 3 substituents selected from $C_{1-6}$ alkyl and $C_{1-6}$ alkoxy is preferable.

As a group represented by the formula:

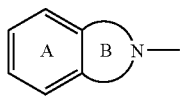

wherein respective symbols are as defined above, groups represented by the formulas:

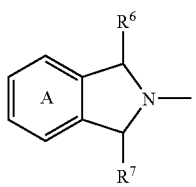 and 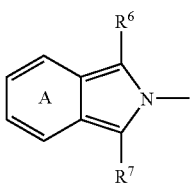

wherein respective symbols are as defined above, are preferable. In particular, $R^6$ and $R^7$ are preferably a hydrogen atom, and the A ring is preferably a benzene ring optionally substituted with 1 to 3 substituents selected from halogen, $C_{1-6}$ alkoxy and $C_{1-6}$ alkylenedioxy.

The position at which the $C^1$ ring is substituted with a group represented by the formula:

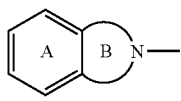

wherein respective symbols are as defined in claim 1, is preferably the 5-position of the benzofuran ring or the dihydrobenzofuran ring.

In particular, the compound (Ia) is preferably a compound in which $R^1$ and $R^2$ are each a hydrogen atom or a $C_{1-6}$ alkyl group (in particular $C_{1-3}$ alkyl group such as methyl), $R^{3a}$ is a hydrogen atom or a phenyl group optionally substituted with 1 to 3 substituents selected from $C_{1-6}$ alkyl (in particular $C_{1-3}$ alkyl such as methyl, ethyl, propyl or isopropyl) and halogen (in particular, fluorine), the A ring is a benzene ring optionally substituted with 1 to 3 substituents selected from halogen, $C_{1-6}$ alkyl (in particular, $C_{1-3}$ alkyl such as methyl), $C_{1-6}$ alkoxy (in particular, $C_{1-3}$ alkoxy such as methoxy) and $C_{1-6}$ alkylenedioxy (in particular, $C_{1-3}$ alkylenedioxy such as methylenedioxy), the B ring is a 5- to 7-membered nitrogen-containing heterocycle optionally substituted with 1 to 2 $C_{1-6}$ alkyl, the $C^1$ ring is a benzene ring optionally further substituted with 1 to 3 substituents selected from $C_{1-6}$ alkyl (in particular, $C_{1-3}$ alkyl such as methyl) and $C_{1-6}$ alkoxy (in particular, $C_{1-3}$ alkoxy such as methoxy), and Y is an oxygen atom, and in particular, preferably a compound in which the group represented by the formula:

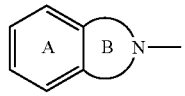

wherein respective symbols are as defined above, is a group represented by the formula:

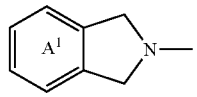

wherein the $A^1$ ring represents a benzene ring optionally substituted with 1 to 3 substituents selected from halogen, $C_{1-6}$ alkoxy and $C_{1-6}$ alkylenedioxy.

When ---- represents a double bond, $R^2$ is not present and $R^1$ is preferably a $C_{1-6}$ alkyl group, more preferably a $C_{1-3}$ alkyl group such as methyl. The other symbols are preferably the same as the above described symbols. Inter alia, preferred is a compound in which $R^{3a}$ is a phenyl group optionally substituted with 1 to 3 $C_{1-6}$ alkyl (in particular, $C_{1-3}$ alkyl such as methyl, ethyl, propyl or isopropyl), the A ring is a benzene ring optionally substituted with 1 to 3 $C_{1-6}$ alkoxy (in particular, methoxy), the B ring is a 5- to 7-membered nitrogen-containing heterocycle, the $C^1$ ring is a benzene ring optionally further substituted with 1 to 3 $C_{1-6}$ alkyl (in particular, $C_{1-3}$ alkyl such as methyl) (in particular, a benzene ring substituted with three $C_{1-6}$ alkyl such as methyl) and Y is an oxygen atom. A compound in which the group represented by the formula:

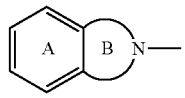

wherein respective symbols are as defined above, is a group represented by the formula:

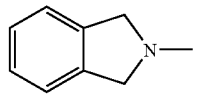

is particularly preferable.

Specific examples of the compound (Ia) include, preferably, the following compound 1a to 22a or salts thereof.

Compound 1a: 2-(2,2,4,6,7-pentamethyl-3-phenyl-2,3-dihydro-1-benzofuran-5-yl)isoindoline Compound 2a: 5,6-dichloro-2-(2,2,4,6,7-pentamethyl-3-phenyl-2,3-dihydro-1-benzofuran-5-yl)isoindoline Compound 3a: 5,6-dimethoxy-2-(2,2,4,6,7-pentamethyl-3-phenyl-2,3-dihydro-1-benzofuran-5-yl)isoindoline Compound 4a: 2-[2,2,4,6,7-pentamethyl-3-(4-methylphenyl)-2,3-dihydro-1-benzofuran-5-yl]isoindoline
Compound 5a: 5,6-dichloro-2-[2,2,4,6,7-pentamethyl-3-(4-methylphenyl)-2,3-dihydro-1-benzofuran-5-yl]isoindoline
Compound 6a: 5,6-dimethoxy-2-[2,2,4,6,7-pentamethyl-3-(4-methylphenyl)-2,3-dihydro-1-benzofuran-5-yl]isoindoline
Compound 7a: 2-[3-(4-fluorophenyl)-2,2,4,6,7-pentamethyl-2,3-dihydro-1-benzofuran-5-yl]isoindoline
Compound 8a: 5,6-dichloro-2-[3-(4-fluorophenyl)-2,2,4,6,7-pentamethyl-2,3-dihydro-1-benzofuran-5-yl]isoindoline
Compound 9a: 2-[3-(4-isopropylphenyl)-2,2,4,6,7-pentamethyl-2,3-dihydro-1-benzofuran-5-yl]isoindoline
Compound 10a: 5,6-dichloro-2-[3-(4-isopropylphenyl)-2,2,4,6,7-pentamethyl-2,3-dihydro-1-benzofuran-5-yl]isoindoline
Compound 11a: 5,6-dimethoxy-2-[3-(4-isopropylphenyl)-2,2,4,6,7-pentamethyl-2,3-dihydro-1-benzofuran-5-yl]isoindoline
Compound 12a: 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole
Compound 13a: 2-[3-(4-isopropylphenyl)-2,4,6,7-tetramethyl-1-benzofuran-5-yl]isoindoline
Compound 14a: 6-[2,2,4,6,7-pentamethyl-3-(4-methylphenyl)-2,3-dihydro-1-benzofuran-5-yl]-6H-[1,3]dioxolo[4,5-f]isoindole
Compound 15a: 2-[2,2,4,6,7-pentamethyl-2,3-dihydro-1-benzofuran-5-yl]isoindoline
Compound 16a: 6-(2,2,4,6,7-pentamethyl-3-phenyl-2,3-dihydro-1-benzofuran-5-yl)-6,7-dihydro-5H-[1,3]dioxolo[4,5-f]isoindole
Compound 17a: (+)-5,6-dimethoxy-2-[2,2,4,6,7-pentamethyl-3-(4-methylphenyl)-2,3-dihydro-1-benzofuran-5-yl]isoindoline
Compound 18a: (−)-5,6-dimethoxy-2-[2,2,4,6,7-pentamethyl-3-(4-methylphenyl)-2,3-dihydro-1-benzofuran-5-yl]isoindoline
Compound 19a: (+)-5,6-dimethoxy-2-[2,2,4,6,7-pentamethyl-3-(4-methylphenyl)-2,3-dihydro-1-benzofuran-5-yl]isoindoline hydrochloride
Compound 20a: (−)-5,6-dimethoxy-2-[2,2,4,6,7-pentamethyl-3-(4-methylphenyl)-2,3-dihydro-1-benzofuran-5-yl]isoindoline hydrochloride
Compound 21a: (+)-5,6-dimethoxy-2-[2,2,4,6,7-pentamethyl-3-(4-methylphenyl)-2,3-dihydro-1-benzofuran-5-yl]isoindoline hydrobromide
Compound 22a: (−)-5,6-dimethoxy-2-[2,2,4,6,7-pentamethyl-3-(4-methylphenyl)-2,3-dihydro-1-benzofuran-5-yl]isoindoline hydrobromide
Compound 23a: 5,6-dimethoxy-2-[2,2,4,6,7-pentamethyl-3-(4-methylphenyl)-2,3-dihydro-1-benzofuran-5-yl]-2H-isoindole.

The chemical structural formulas of the compounds 1a to 23a are shown below.

TABLE 1

| Compound No. | a | b | c | d | e | f | g | = |
|---|---|---|---|---|---|---|---|---|
| 1a | Me | Me | phenyl | Me | isoindoline | Me | Me | — |
| 2a | Me | Me | phenyl | Me | 5,6-dichloroisoindoline | Me | Me | — |
| 3a | Me | Me | phenyl | Me | 5,6-dimethoxyisoindoline | Me | Me | — |
| 4a | Me | Me | 4-methylphenyl | Me | isoindoline | Me | Me | — |
| 5a | Me | Me | 4-methylphenyl | Me | 5,6-dichloroisoindoline | Me | Me | — |

TABLE 1-continued
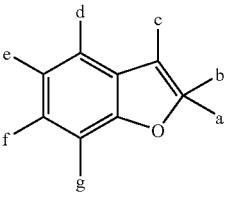
| Compound No. | a | b | c | d | e | f | g | = |
|---|---|---|---|---|---|---|---|---|
| 6a | Me | Me | 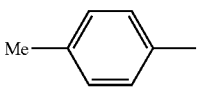 | Me | 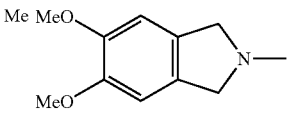 | Me | Me | — |
| 7a | Me | Me | 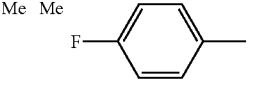 | Me | 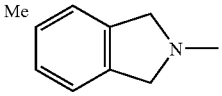 | Me | Me | — |
| 8a | Me | Me | 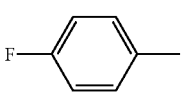 | Me | 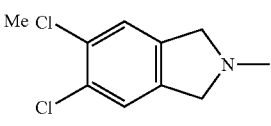 | Me | Me | — |
| 9a | Me | Me | 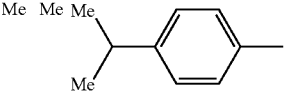 | Me | 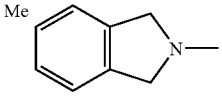 | Me | Me | — |
| 10a | Me | Me | 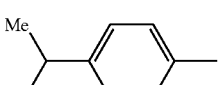 | Me | 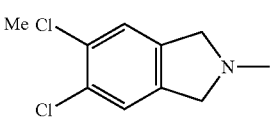 | Me | Me | — |
| 11a | Me | Me | 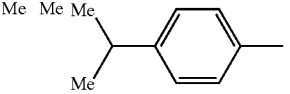 | Me | 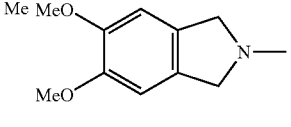 | Me | Me | — |
| 12a | Me | Me | 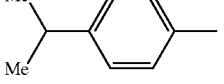 | Me | 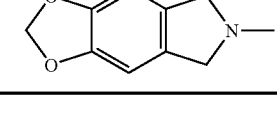 | Me | Me | — |
TABLE 2
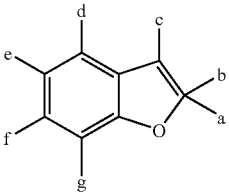
| Compound No. | a | b | c | d | e | f | g | = | Adduct |
|---|---|---|---|---|---|---|---|---|---|
| 13a | Me | — | 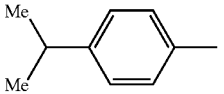 | Me | 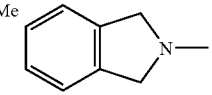 | Me | Me | = | |

TABLE 2-continued

[Benzofuran core structure with positions labeled a, b, c, d, e, f, g]

| Compound No. | a | b | c | d | e | f | g | = | Adduct |
|---|---|---|---|---|---|---|---|---|---|
| 14a | Me | Me | [p-tolyl-Me] | Me | [methylenedioxy-isoindoline] | Me | Me | — | |
| 15a | Me | Me | H | | [isoindoline] | Me | Me | — | |
| 16a | Me | Me | [phenyl] | Me | [methylenedioxy-isoindoline] | Me | Me | — | |
| 17a | Me | Me | [p-tolyl-Me]* | Me | [5,6-dimethoxy-isoindoline] | Me | Me | — | |
| 18a | Me | Me | [p-tolyl-Me]* | Me | [5,6-dimethoxy-isoindoline] | Me | Me | — | |
| 19a | Me | Me | [p-tolyl-Me]* | Me | [5,6-dimethoxy-isoindoline] | Me | Me | — | HCl |
| 20a | Me | Me | [p-tolyl-Me]* | Me | [5,6-dimethoxy-isoindoline] | Me | Me | — | HCl |
| 21a | Me | Me | [p-tolyl-Me]* | Me | [5,6-dimethoxy-isoindoline] | Me | Me | — | HBr |
| 22a | Me | Me | [p-tolyl-Me]* | Me | [5,6-dimethoxy-isoindoline] | Me | Me | — | HBr |
| 23a | Me | Me | [p-tolyl-Me]* | Me | [5,6-dimethoxy-isoindole] | Me | Me | — | |

As the compound (Ia), inter alia, preferred are:

[1] 2-[2,2,4,6,7-pentamethyl-3-(4-methylphenyl)-2,3-dihydro-1-benzofuran-5-yl]isoindoline (Compound 4a) or a salt thereof;

[2] 5,6-dimethoxy-2-[2,2,4,6,7-pentamethyl-3-(4-methylphenyl)-2,3-dihydro-1-benzofuran-5-yl]isoindoline (Compound 6a) or a salt thereof, inter alia, an optically active form thereof, (R)-(+)-5,6-dimethoxy-2-[2,2,4,6,7-pentamethyl-3-(4-methylphenyl)-2,3-dihydro-1-benzofuran-5-yl]isoindoline (or also referred as (R)-5,6-dimethoxy-2-[2,2,4,6,7-pentamethyl-3-(4-methylphenyl)benzofuran-5-yl]-2,3-dihydro-1H-isoindole) or a salt thereof;

[3] 5,6-dimethoxy-2-[3-(4-isopropylphenyl)-2,2,4,6,7-pentamethyl-2,3-dihydro-1-benzofuran-5-yl]isoindoline (Compound 11a) or a salt thereof, inter alia, (R)-(+)-5,6-dimethoxy-2-[2,2,4,6,7-pentamethyl-3-(4-(1-methylethyl)phenyl)-2,3-dihydro-1-benzofuran-5-yl]isoindoline or a salt thereof;

[4] 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole (Compound 12a) or a salt thereof;

[5] 6-[2,2,4,6,7-pentamethyl-3-(4-methylphenyl)-2,3-dihydro-1-benzofuran-5-yl]-6H-[1,3]dioxolo[4,5-f]isoindole (Compound 14a) or a salt thereof;

[6] 6-(2,2,4,6,7-pentamethyl-3-phenyl-2,3-dihydro-1-benzofuran-5-yl)-6,7-dihydro-5H-[1,3]dioxolo[4,5-f]isoindole (Compound 16a) or a salt thereof;

[7] (R)-5,6-dimethoxy-2-[2,2,4,6,7-pentamethyl-3-(4-methylphenyl)-2,3-dihydro-1-benzofuran-5-yl]isoindoline (Compound 17a);

[8] (R)-5,6-dimethoxy-2-[2,2,4,6,7-pentamethyl-3-(4-methylphenyl)-2,3-dihydro-1-benzofuran-5-yl]isoindoline hydrochloride (Compound 19a); and

[9] 5,6-dimethoxy-2-[2,2,4,6,7-pentamethyl-3-(4-methylphenyl)-2,3-dihydro-1-benzofuran-5-yl]-2H-isoindole (Compound 23a) or a salt thereof, and more preferred are:

[1] 5,6-dimethoxy-2-[2,2,4,6,7-pentamethyl-3-(4-methylphenyl)-2,3-dihydro-1-benzofuran-5-yl]isoindoline (Compound 6a);

[2] 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole (Compound 12a);

[3] (R)-5,6-dimethoxy-2-[2,2,4,6,7-pentamethyl-3-(4-methylphenyl)-2,3-dihydro-1-benzofuran-5-yl]isoindoline (Compound 17a);

[4] (R)-5,6-dimethoxy-2-[2,2,4,6,7-pentamethyl-3-(4-methylphenyl)-2,3-dihydro-1-benzofuran-5-yl]isoindoline hydrochloride (Compound 19a); and

[5] 5,6-dimethoxy-2-[2,2,4,6,7-pentamethyl-3-(4-methylphenyl)-2,3-dihydro-1-benzofuran-5-yl]-2H-isoindole (Compound 23a).

In the above compound (Ib), preferably $R^1$ and $R^2$ are the same or different and are each a hydrogen atom or an optionally substituted $C_{1-6}$ alkyl group (particularly, $C_{1-3}$ alkyl group such as methyl), or $R^1$ and $R^2$ are taken together with the adjacent carbon atom to form an optionally substituted 3- to 8-membered homocycle (e.g. $C_{3-8}$ cycloalkane such as cyclopropane, cyclobutane, cyclopentane, cyclohexane etc.), and more preferably $R^1$ and $R^2$ are the same or different and are each a hydrogen atom or a $C_{1-6}$ alkyl group (particularly, $C_{1-3}$ alkyl group such as methyl), or $R^1$ and $R^2$ are taken together with the adjacent carbon atom to form a 3- to 8-membered homocycle. Inter alia, $R^1$ and $R^2$ are more preferably each a $C_{1-6}$ alkyl group, and $R^1$ and $R^2$ are especially preferably each a methyl group.

$R^{3b}$ is preferably, for example, a phenyl group optionally substituted with 1 to 3 substituents selected from halogen (in particularly, fluorine) and $C_{1-6}$ alkyl (in particular, $C_{1-3}$ alkyl such as methyl, ethyl, propyl or isopropyl), and more preferably a phenyl group optionally substituted with fluorine, methyl or isopropyl.

$R^4$ is preferably, for example, (1) a $C_{1-6}$ alkyl group substituted with an aromatic group (in particular, a $C_{6-14}$ aryl group such as phenyl or a 5- or 6-membered aromatic heterocyclic group containing 1 to 3 hetero atoms selected from a nitrogen atom, an oxygen atom and a sulfur atom in addition to carbon atoms, such as thienyl and pyridyl) optionally substituted with 1 to 3 substituents selected from halogen, $C_{1-6}$ alkoxy and $C_{1-3}$ alkylenedioxy, or (2) an acyl group containing an aromatic group (in particular, $C_{6-14}$ aryl group such as phenyl) optionally substituted with 1 to 3 substituents selected from halogen, $C_{1-6}$ alkoxy and $C_{1-3}$ alkylenedioxy, and more preferably (1) a $C_{1-6}$ alkyl group (in particular, $C_{1-3}$ alkyl group such as methyl) substituted with $C_{6-14}$ aryl (in particular, phenyl), thienyl or pyridyl optionally substituted with 1 to 3 substituents selected from halogen (in particular, fluorine or chlorine), $C_{1-6}$ alkoxy (in particular, $C_{1-3}$ alkoxy such as methoxy) and $C_{1-3}$ alkylenedioxy (in particular, methylenedioxy), or (2) a $C_{6-14}$ aryl-carbonyl group (in particular, a phenylcarbonyl group), a $C_{7-16}$ aralkyl-carbonyl group (in particular, a benzylcarbonyl group), a $C_{6-14}$ aryl-sulfonyl group (in particular, a phenylsulfonyl group), a nicotinoyl group or a thenoyl group, each of which may be optionally substituted with 1 to 3 substituents selected from halogen (in particular, fluorine or chlorine), $C_{1-6}$ alkoxy (in particular, $C_{1-3}$ alkoxy such as methoxy) and $C_{1-3}$ alkylenedioxy (in particular, methylenedioxy). Inter alia, especially preferred is a benzyl group or a phenethyl group each of which may be optionally substituted with 1 to 3 substituents selected from fluorine, methoxy and methylenedioxy.

$R^5$ is preferably, for example, a hydrogen atom, a $C_{1-6}$ alkyl group (in particular, $C_{1-3}$ alkyl group such as methyl) or a $C_{1-6}$ alkyl-carbonyl group (in particular, $C_{1-3}$ alkyl-carbonyl group such as acetyl), and more preferably a hydrogen atom or a methyl group.

The $C^2$ ring is preferably a benzene ring optionally further substituted with 1 to 3 $C_{1-6}$ alkyl (in particular, $C_{1-3}$ alkyl such as methyl) and more preferably a benzene ring further substituted with three methyl.

In particular, the compound (Ib) is preferably a compound in which $R^1$ and $R^2$ are the same or different and are each a hydrogen atom or a $C_{1-6}$ alkyl group (in particular, $C_{1-3}$ alkyl group such as methyl), or $R^1$ and $R^2$ are taken together with the adjacent carbon atom to form a 3- to 8-membered homocycle;

$R^{3b}$ is a phenyl group optionally substituted with 1 to 3 substituents selected from halogen (in particular, fluorine) and $C_{1-6}$ alkyl (in particular, $C_{1-3}$ alkyl such as methyl, ethyl, propyl or isopropyl);

$R^4$ is (1) a $C_{1-6}$ alkyl group (in particular, $C_{1-3}$ alkyl group such as methyl) substituted with $C_{6-14}$ aryl (in particular, phenyl), thienyl or pyridyl each of which may be optionally substituted with 1 to 3 substituents selected from halogen (in particular, fluorine or chlorine), $C_{1-6}$ alkoxy (in particular, $C_{1-3}$ alkoxy group such as methoxy) and $C_{1-3}$ alkylenedioxy (in particular, methylenedioxy), or (2) a $C_{6-14}$ aryl-carbonyl group (in particular, a phenylcarbonyl group), a $C_{7-16}$ aryl-carbonyl group (in particular, a benzylcarbonyl group), a $C_{6-14}$ aryl-sulfonyl group (in particular, a phenylsulfonyl group), a nicotinoyl group or a thenoyl group each of which may be optionally substituted with 1 to 3 substituents selected from halogen (in particular, fluorine or chlorine), $C_{1-6}$ alkoxy (in particular, $C_{1-3}$ alkoxy group such as methoxy) and $C_{1-3}$ alkylenedioxy (in particular, methylendioxy);

$R^5$ is a hydrogen atom, a $C_{1-6}$ alkyl group (in particular, a $C_{1-3}$ alkyl group such as methyl) or a $C_{1-6}$ alkyl-carbonyl group (in particular, a $C_{1-3}$ alkyl-carbonyl group such as acetyl);

Y is an oxygen atom; and the $C^2$ ring is a benzene ring further substituted with 1 to 3 $C_{1-6}$ alkyl (in particular, $C_{1-3}$ alkyl such as methyl), and more preferably a compound in which $R^1$ and $R^2$ are each a methyl group;

$R^{3b}$ is a phenyl group optionally substituted with fluorine, methyl or isopropyl;

$R^4$ is a benzyl or phenethyl group optionally substituted with fluorine, methoxy or methylenedioxy;

$R^5$ is a hydrogen atom or a methyl group;

--- is a single bond;

Y is an oxygen atom; and the $C^2$ ring is a benzene ring further substituted with three methyl.

When --- represents a double bond, $R^2$ is not present and $R^1$ is preferably a $C_{1-6}$ alkyl group and more preferably a $C_{1-3}$ alkyl group such as methyl. The other symbols are preferably the same as the above described symbols and, inter alia, preferred is a compound in which $R^{3b}$ is a phenyl group optionally substituted with 1 to 3 substituens selected from halogen (in particular fluorine) and $C_{1-6}$ alkyl (in particular, $C_{1-3}$ alkyl such as methyl, ethyl, propyl or isopropyl); $R^4$ is (1) a $C_{1-6}$ alkyl group (in particular, $C_{1-3}$ alkyl group such as methyl) which is substituted with $C_{6-14}$ aryl (in particular, phenyl) optionally substituted with 1 to 3 substituents selected from halogen (in particular, fluorine) and $C_{1-6}$ alkoxy (in particular, $C_{1-3}$ alkoxy group such as methoxy), or (2) a $C_{6-14}$ aryl-carbonyl group (in particular, a phenylcarbonyl group) or a $C_{7-16}$ aralkyl-carbonyl group (in particular, a benzylcarbonyl group) each of which may be optionally substituted with 1 to 3 substituents selected from halogen (in particular, fluorine) and $C_{1-6}$ alkoxy (in particular, $C_{1-3}$ alkoxy group such as methoxy); $R^5$ is a hydrogen atom; Y is an oxygen atom; and the $C^2$ ring is a benzene ring further substituted with 1 to 3 $C_{1-6}$ alkyl (in particular, $C_{1-3}$ alkyl such as methyl)(in particular, a benzene ring substituted with three $C_{1-6}$ alkyl such as methyl).

Specific examples of the compound (Ib) include preferably the following Compounds 1b to 67b.

Compound 1b: 4-methoxy-N-(2,2,4,6,7-pentamethyl-3-phenyl-2,3-dihydro-1-benzofuran-5-yl)benzamide Compound 2b: N-(4-methoxybenzyl)-2,2,4,6,7-pentamethyl-3-phenyl-2,3-dihydro-1-benzofuran-5-amine Compound 3b: 4-fluoro-N-(2,2,4,6,7-pentamethyl-3-phenyl-2,3-dihydro-1-benzofuran-5-yl)benzamide Compound 4b: N-(4-fluorobenzyl)-2,2,4,6,7-pentamethyl-3-phenyl-2,3-dihydro-1-benzofuran-5-amine Compound 5b: N-[3-(4-isopropylphenyl)-2,2,4,6,7-pentamethyl-2,3-dihydro-1-benzofuran-5-yl]benzamide Compound 6b: N-benzyl-3-(4-isopropylphenyl)-2,2,4,6,7-pentamethyl-2,3-dihydro-1-benzofuran-5-amine hydrochloride Compound 7b: N-[3-(4-isopropylphenyl)-2,2,4,6,7-pentamethyl-2,3-dihydro-1-benzofuran-5-yl]-4-methoxybenzamide Compound 8b: 3-(4-isopropylphenyl)-N-(4-methoxybenzyl)-2,2,4,6,7-pentamethyl-2,3-dihydro-1-benzofuran-5-amine Compound 9b: 3-(4-isopropylphenyl)-N-(4-methoxybenzyl)-N,2,2,4,6,7-hexamethyl-2,3-dihydro-1-benzofuran-5-amine Compound 10b: N-[3-(4-isopropylphenyl)-2,2,4,6,7-pentamethyl-2,3-dihydro-1-benzofuran-5-yl]-4-methoxyphenylacetamide Compound 11b: 3-(4-isopropylpheny)-N-[2-(4-methoxyphenyl)ethyl]-2,2,4,6,7-pentamethyl-2,3-dihydro-1-benzofuran-5-amine Compound 12b: 3-(4-isopropylphenyl)-N-[2-(4-methoxyphenyl)ethyl]-N,2,2,4,6,7-hexamethyl-2,3-dihydro-1-benzofuran-5-amine Compound 13b: N-[3-(4-isopropylphenyl)-2,2,4,6,7-pentamethyl-2,3-dihydro-1-benzofuran-5-yl]-N-[2-(4-methoxyphenyl)ethyl]acetamide Compound 14b: N-[3-(4-isopropylphenyl)-2,2,4,6,7-pentamethyl-2,3-dihydro-1-benzofuran-5-yl]-N-[2-(4-methoxyphenyl)ethyl]acetamide Compound 15b: N-[3-(4-isopropylphenyl)-2,2,4,6,7-pentamethyl-2,3-dihydro-1-benzofuran-5-yl]-3-(4-methoxyphenyl)propionamide Compound 16b: 3-(4-isopropylphenyl)-N-[3-(4-methoxyphenyl)propyl]-2,2,4,6,7-pentamethyl-2,3-dihydro-1-benzofuran-5-amine Compound 17b: N-[3-(4-isopropylphenyl)-2,2,4,6,7-pentamethyl-2,3-dihydro-1-benzofuran-5-yl]-4-methoxybenzenesulfonamide Compound 18b: 4-fluoro-N-[3-(4-isopropylphenyl)-2,2,4,6,7-pentamethyl-2,3-dihydro-1-benzofuran-5-yl]benzamide Compound 19b: N-(4-fluorobenzyl)-3-(4-isopropylphenyl)-2,2,4,6,7-pentamethyl-2,3-dihydro-1-benzofuran-5-amine hydrochloride Compound 20b: 4-chloro-N-[3-(4-isopropylphenyl)-2,2,4,6,7-pentamethyl-2,3-dihydro-1-benzofuran-5-yl]benzamide Compound 21b: N-(4-chlorobenzyl)-3-(4-isopropylphenyl)-2,2,4,6,7-pentamethyl-2,3-dihydro-1-benzofuran-5-amine Compound 22b: N-[3-(4-isopropylphenyl)-2,2,4,6,7-pentamethyl-2,3-dihydro-1-benzofuran-5-yl]-1,3-benzodioxol-5-carboxyamide Compound 23b: N-(1,3-benzodioxol-5-ylmethyl)-3-(4-isopropylphenyl)-2,2,4,6,7-pentamethyl-2,3-dihydro-1-benzofuran-5-amine Compound 24b: N-[3-(4-isopropylphenyl)-2,2,4,6,7-pentamethyl-2,3-dihydro-1-benzofuran-5-yl]-2-thiophenecarboxyamide Compound 25b: 3-(4-isopropylphenyl)-2,2,4,6,7-pentamethyl-N-(2-thienylmethyl)-2,3-dihydro-1-benzofuran-5-amine Compound 26b: N-[3-(4-isopropylphenyl)-2,2,4,6,7-pentamethyl-2,3-dihydro-1-benzofuran-5-yl]nicotinamide Compound 27b: N-[3-(4-isopropylphenyl)-2,2,4,6,7-pentamethyl-2,3-dihydro-1-benzofuran-5-yl]isonicotinamide hydrochloride Compound 28b: N-[3-(4-fluorophenyl)-2,2,4,6,7-pentamethyl-2,3-dihydro-1-benzofuran-5-yl]-4-methoxybenzamide Compound 29b: 3-(4-fluorophenyl)-N-(4-methoxybenzyl)-2,2,4,6,7-pentamethyl-2,3-dihydro-1-benzofuran-5-amine Compound 30b: 4-fluoro-N-[3-(4-fluorophenyl)-2,2,4,6,7-pentamethyl-2,3-dihydro-1-benzofuran-5-yl]benzamide Compound 31b: N-(4-fluorobenzyl)-3-(4-fluorophenyl)-2,2,4,6,7-pentamethyl-2,3-dihydro-1-benzofuran-5-amine Compound 32b: 4-methoxy-N-[2,2,4,6,7-pentamethyl-3-(4-methylphenyl)-2,3-dihydro-1-benzofuran-5-yl]benzamide Compound 33b: N-(4-methoxybenzyl)-2,2,4,6,7-pentamethyl-3-(4-methylphenyl)-2,3-dihydro-1-benzofuran-5-amine Compound 34b: 4-fluoro-N-[2,2,4,6,7-pentamethyl-3-(4-methylphenyl)-2,3-dihydro-1-benzofuran-5-yl]benzamide Compound 35b: N-(4-fluorobenzyl)-2,2,4,6,7-pentamethyl-3-(4-methylphenyl)-2,3-dihydro-1-benzofuran-5-amine Compound 36b: methyl 4-[[3-(4-isopropylphenyl)-2,2,4,6,7-pentamethyl-2,3-dihydro-1-benzofuran-5-ylamino]carbonyl]benzoate Compound 37b: 4-[[3-(4-isopropylphenyl)-2,2,4,6,7-pentamethyl-2,3-dihydro-1-benzofuran-5-ylamino]carbonyl]benzoic acid Compound 38b: 5-(4-methoxybenzylamino)-2,4,6,7-tetramethyl-3-phenyl-1-benzofuran hydrochloride Compound 39b: 4-fluoro-N-(2,4,6,7-tetramethyl-3-phenyl-1-benzofuran-5-yl)benzamide Compound 40b: N-(4-fluorobenzyl)-2,4,6,7-tetramethyl-3-phenyl-1-benzofuran-5-amine Compound 41b: N-[3-(4-isopropylphenyl)-2,4,6,7-tetramethyl-1-benzofuran-5-yl]benzamide Compound 42b: N-benzyl-3-(4-isopropylphenyl)-2,4,6,7-tetramethyl-1-benzofuran-5-amine Compound 43b: [N-[3-(4-isopropylphenyl)-2,4,6,7-tetramethyl-1-benzofuran-5-yl]]-4-methoxybenzamide Compound 44b: [N-[3-(4-isopropylphenyl)-2,4,6,7-tetramethyl-1-benzofuran-5-yl]]-4-methoxyphenylacetamide Compound 45b: 3-(4-isopropylphenyl)-N-(4-methoxybenzyl)-2,4,6,7-tetramethyl-1-benzofuran-5-amine hydrochloride Compound 46b: 4-fluoro-N-[3-(4-isopropylphenyl)-2,4,6,7-tetramethyl-1-benzofuran-5-yl]benzamide Compound 47b: N-(4-fluorobenzyl)-3-(4-isopropylphenyl)-2,4,6,7-tetramethyl-1-benzofuran-5-amine Compound 48b: N-[3-(4-fluorophenyl)-2,4,6,7-tetramethyl-1-benzofuran-5-yl]-4-methoxybenzamide Compound 49b: N-(4-methoxybenzyl)-3-(4-fluorophenyl)-2,4,6,7-tetramethyl-1-benzofuran-5-amine Compound 50b: 4-fluoro-N-[3-(4-fluorophenyl)-2,4,6,7-tetramethyl-1-benzofuran-5-yl]benzamide Compound 51b: N-(4-fluorobenzyl)-3-(4-fluorophenyl)-2,4,6,7-tetramethyl-1-benzofuran-5-amine Compound 52b: N-[3-(4-isopropylphenyl)-1',4,6,7-tetramethylspiro[benzofuran-2(3H), 4'-piperidine]-5-yl]-4-methoxybenzamide Compound 53b: 3-(4-isopropylphenyl)-N-(4-methoxybenzyl)-1',4,6,7-tetramethylspiro[benzofuran-2(3H), 4'-piperidine]-5-amine Compound 54b: 4-fluoro-N-[3-(4-isopropylphenyl)-1',4,6,7-tetramethylspiro[benzofuran-2(3H), 4'-piperidine]-5-yl]benzamide Compound 55b: N-(4-fluorobenzyl)-3-(4-isopropylphenyl)-1',4,6,7-tetramethylspiro[benzofuran-2(3H), 4'-piperidine]-5-amine Compound 56b: 4-chloro-N-[3-(4-isopropylphenyl)-1',4,6,7-tetramethylspiro[benzofuran-2(3H), 4'-piperidine]-5-yl]benzamide Compound 57b: N-(4-chlorobenzyl)-3-(4-isopropylphenyl)-1',4,6,7-tetramethylspiro[benzofuran-2(3H), 4'-piperidine]-5-amine Compound 58b: N-[3-(4-isopropylphenyl)-2,2,4,6,7-pentamethyl-2,3-dihydro-1-benzofuran-5-yl]-3,4-dimethoxybenzamide Compound 59b: N-(3,4-dimethoxybenzyl)-3-(4-isopropylphenyl)-2,2,4,6,7-pentamethyl-2,3-dihydro-1-benzofuran-5-amine hydrochloride Compound 60b: (+)-4-fluoro-N-[3-(4-isopropylphenyl)-2,2,4,6,7-pentamethyl-2,3-dihydro-1-benzofuran-5-yl]benzamide Compound 61b: (+)-N-(4-fluorobenzyl)-3-(4-isopropylphenyl)-2,2,4,6,7-pentamethyl-2,3-dihydro-1-benzofuran-5-amine hydrochloride Compound 62b: (−)-4-fluoro-N-[3-(4-isopropylphenyl)-2,2,4,6,7-pentamethyl-2,3-dihydro-1-benzofuran-5-yl]benzamide Compound 63b: (−)-N-(4-fluorobenzyl)-3-(4-isopropylphenyl)-2,2,4,6,7-pentamethyl-2,3-dihydro-1-benzofuran-5-amine hydrochloride Compound 64b: 3,4-dimethoxy-N-[2,2,4,6,7-pentamethyl-3-(4-methylphenyl)-2,3-dihydro-1-benzofuran-5-yl]benzamide Compound 65b: N-(3,4-dimethoxybenzyl)-2,2,4,6,7-pentamethyl-3-(4-methylphenyl)-2,3-dihydro-1-benzofuran-5-amine hydrochloride Compound 66b: N-[2,2,4,6,7-pentamethyl-3-(4-methylphenyl)-2,3-dihydro-1-benzofuran-5-yl]-1,3-benzodioxol-5-carboxamide Compound 67b: N-(1,3-benzodioxol-5-ylmethyl)-2,2,4,6,7-pentamethyl-3-(4-methylphenyl)-2,3-dihydro-1-benzofuran-5-amine hydrochloride.

The chemical structural formulas of the Compounds 1b to 66b are shown below:

TABLE 3

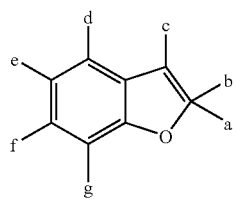

| Compound No. | a | b | c | d | e | f | g | = |
|---|---|---|---|---|---|---|---|---|
| 1b | Me | Me | (phenyl) | Me | H₃CO-C₆H₄-C(=O)NH | Me | Me | — |

TABLE 3-continued

Benzofuran scaffold with positions a, b (C2); c (C3); d, e (C5); f (C6); g (C7).

| Compound No. | a | b | c | d | e | f | g | = |
|---|---|---|---|---|---|---|---|---|
| 2b | Me | Me | phenyl | Me | 4-H₃CO-C₆H₄-CH₂NH- | Me | Me | — |
| 3b | Me | Me | phenyl | Me | 4-F-C₆H₄-C(O)NH- | Me | Me | — |
| 4b | Me | Me | phenyl | Me | 4-F-C₆H₄-CH₂NH- | Me | Me | — |
| 5b | Me | Me | 4-(CH(Me)₂)-C₆H₄- | Me | C₆H₅-C(O)NH- | Me | Me | — |
| 6b | Me | Me | 4-(CH(Me)₂)-C₆H₄- | Me | C₆H₅-CH₂NH- | Me | Me | — |
| 7b | Me | Me | 4-(CH(Me)₂)-C₆H₄- | Me | 4-H₃CO-C₆H₄-C(O)NH- | Me | Me | — |
| 8b | Me | Me | 4-(CH(Me)₂)-C₆H₄- | Me | 4-H₃CO-C₆H₄-CH₂NH- | Me | Me | — |
| 9b | Me | Me | 4-(CH(Me)₂)-C₆H₄- | Me | 4-H₃CO-C₆H₄-CH₂NCH₃- | Me | Me | — |
| 10b | Me | Me | 4-(CH(Me)₂)-C₆H₄- | Me | 4-H₃CO-C₆H₄-CH₂C(O)NH- | Me | Me | — |
| 11b | Me | Me | 4-(CH(Me)₂)-C₆H₄- | Me | 4-H₃CO-C₆H₄-CH₂CH₂NH- | Me | Me | — |
| 12b | Me | Me | 4-(CH(Me)₂)-C₆H₄- | Me | 4-H₃CO-C₆H₄-CH₂CH₂NCH₃- | Me | Me | — |

TABLE 3-continued

[Benzofuran core structure with positions a, b, c, d, e, f, g]

| Compound No. | a | b | c | d | e | f | g | = |
|---|---|---|---|---|---|---|---|---|
| 13b | Me | Me | Me, CH(Me)-C6H4- | Me | H3CO-C6H4-CH2CH2-N*Ac | Me | Me | — |
| 14b | Me | Me | Me, CH(Me)-C6H4- | Me | H3CO-C6H4-CH2CH2-N*Ac | Me | Me | — |
| 15b | Me | Me | Me, CH(Me)-C6H4- | Me | H3CO-C6H4-CH2CH2-C(O)NH- | Me | Me | — |
| 16b | Me | Me | Me, CH(Me)-C6H4- | Me | H3CO-C6H4-CH2CH2CH2-NH- | Me | Me | — |
| 17b | Me | Me | Me, CH(Me)-C6H4- | Me | H3CO-C6H4-SO2NH- | Me | Me | — |

TABLE 4

[Benzofuran core structure with positions a, b, c, d, e, f, g]

| Compound No. | a | b | c | d | e | f | g | = |
|---|---|---|---|---|---|---|---|---|
| 18b | Me | Me | Me, CH(Me)-C6H4- | Me | F-C6H4-C(O)NH- | Me | Me | — |
| 19b | Me | Me | Me, CH(Me)-C6H4- | Me | F-C6H4-CH2NH- | Me | Me | — |
| 20b | Me | Me | Me, CH(Me)-C6H4- | Me | Cl-C6H4-C(O)NH- | Me | Me | — |

TABLE 4-continued
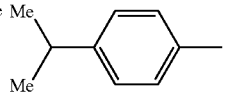
| Compound No. | a | b | c | d | e | f | g | = |
|---|---|---|---|---|---|---|---|---|
| 21b | Me | Me | Me<br>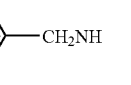 | Me | 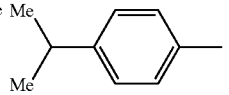 | Me | Me | — |
| 22b | Me | Me | Me<br>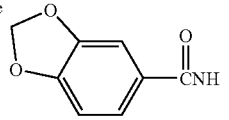 | Me | 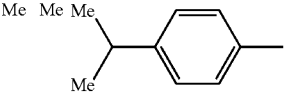 | Me | Me | — |
| 23b | Me | Me | Me<br>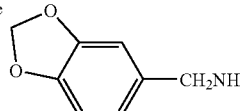 | Me | 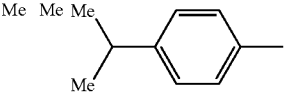 | Me | Me | — |
| 24b | Me | Me | Me<br>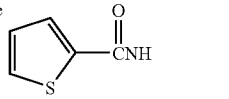 | Me | 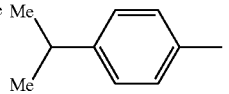 | Me | Me | — |
| 25b | Me | Me | Me<br>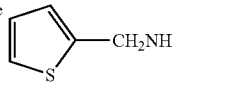 | Me | 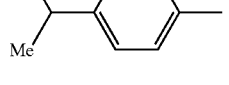 | Me | Me | — |
| 26b | Me | Me | Me<br>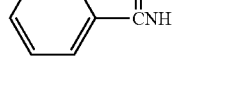 | Me | 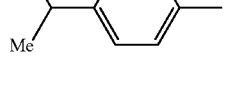 | Me | Me | — |
| 27b | Me | Me | Me<br>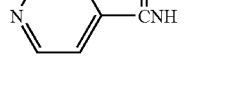 | Me | 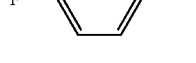 | Me | Me | — |
| 28b | Me | Me | 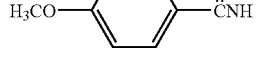 | Me | 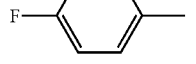 | Me | Me | — |
| 29b | Me | Me | 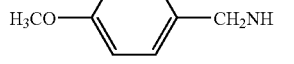 | Me |  | Me | Me | — |
| 30b | Me | Me | 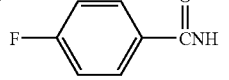 | Me |  | Me | Me | — |
| 31b | Me | Me | 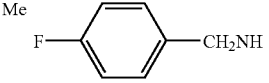 | Me | | Me | Me | — |

TABLE 4-continued

Structure: benzofuran with positions a, b on the 2-position carbon; c on 3-position; d, e, f, g on benzene ring (4, 5, 6, 7 positions respectively)

| Compound No. | a | b | c | d | e | f | g | = |
|---|---|---|---|---|---|---|---|---|
| 32b | Me | Me | 4-Me-C₆H₄- | Me | 4-H₃CO-C₆H₄-C(O)NH- | Me | Me | — |
| 33b | Me | Me | 4-Me-C₆H₄- | Me | 4-H₃CO-C₆H₄-CH₂NH- | Me | Me | — |
| 34b | Me | Me | 4-Me-C₆H₄- | Me | 4-F-C₆H₄-C(O)NH- | Me | Me | — |

TABLE 5

Same benzofuran core structure

| Compound No. | a | b | c | d | e | f | g | = |
|---|---|---|---|---|---|---|---|---|
| 35b | Me | Me | 4-Me-C₆H₄- | Me | 4-F-C₆H₄-CH₂NH- | Me | Me | — |
| 36b | Me | Me | 4-(Me₂CH)-C₆H₄- | Me | 4-H₃COOC-C₆H₄-C(O)NH- | Me | Me | — |
| 37b | Me | Me | 4-(Me₂CH)-C₆H₄- | Me | 4-HOOC-C₆H₄-C(O)NH- | Me | Me | — |
| 38b | Me | — | C₆H₅- | Me | 4-H₃CO-C₆H₄-CH₂NH- | Me | Me | = |
| 39b | Me | — | C₆H₅- | Me | 4-F-C₆H₄-C(O)NH- | Me | Me | = |
| 40b | Me | — | C₆H₅- | Me | 4-F-C₆H₄-CH₂NH- | Me | Me | = |

TABLE 5-continued
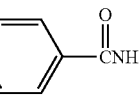
| Compound No. | a | b | c | d | e | f | g | = |
|---|---|---|---|---|---|---|---|---|
| 41b | Me | — | 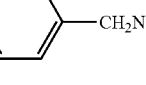 | Me | 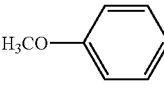 | Me | Me | = |
| 42b | Me | — | 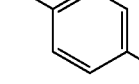 | Me | 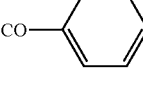 | Me | Me | = |
| 43b | Me | — | 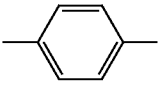 | Me | 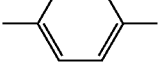 | Me | Me | = |
| 44b | Me | — | 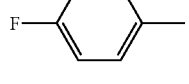 | Me | 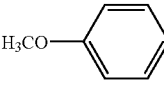 | Me | Me | = |
| 45b | Me | — | 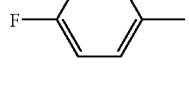 | Me | 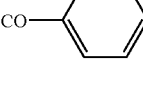 | Me | Me | = |
| 46b | Me | — | 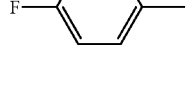 | Me | 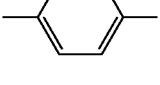 | Me | Me | = |
| 47b | Me | — | 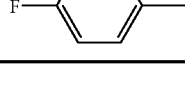 | Me | 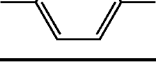 | Me | Me | = |
| 48b | Me | — | 4-F-C6H4- | Me | 4-MeO-C6H4-C(O)NH- | Me | Me | = |
| 49b | Me | — | 4-F-C6H4- | Me | 4-MeO-C6H4-CH2NH- | Me | Me | = |
| 50b | Me | — | 4-F-C6H4- | Me | 4-F-C6H4-C(O)NH- | Me | Me | = |
| 51b | Me | — | 4-F-C6H4- | Me | 4-F-C6H4-CH2NH- | Me | Me | = |

TABLE 6

[Structure: benzofuran-spiro-piperidine with positions c (3), d (4), e (5), f (6), g (7), h (N-substituent)]

| Compound No. | c | d | e | f | g | h |
|---|---|---|---|---|---|---|
| 52b | Me-CH(Me)-C6H4- | Me | 4-H3CO-C6H4-C(=O)NH- | Me | Me | Me |
| 53b | Me-CH(Me)-C6H4- | Me | 4-H3CO-C6H4-CH2NH- | Me | Me | Me |
| 54b | Me-CH(Me)-C6H4- | Me | 4-F-C6H4-C(=O)NH- | Me | Me | Me |
| 55b | Me-CH(Me)-C6H4- | Me | 4-F-C6H4-CH2NH- | Me | Me | Me |
| 56b | Me-CH(Me)-C6H4- | Me | 4-Cl-C6H4-C(=O)NH- | Me | Me | Me |
| 57b | Me-CH(Me)-C6H4- | Me | 4-Cl-C6H4-CH2NH- | Me | Me | Me |

TABLE 7

[Structure: benzofuran with positions a (2), b (2), c (3), d (4), e (5), f (6), g (7)]

| Compound No. | a | b | c | d | e | f | g | Optical activity |
|---|---|---|---|---|---|---|---|---|
| 58b | Me | Me | Me | Me-CH(Me)-C6H4- | Me | 3,4-(H3CO)2-C6H3-C(=O)NH- | Me | Me | — |
| 59b | Me | Me | Me | Me-CH(Me)-C6H4- | Me | 3,4-(H3CO)2-C6H3-CH2NH- | Me | Me | — |

TABLE 7-continued

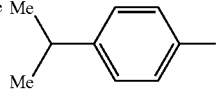

| Compound No. | a | b | c | d | e | f | g | = | Optical activity |
|---|---|---|---|---|---|---|---|---|---|
| 60b | Me | Me | Me, 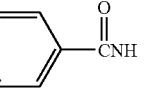 | Me | 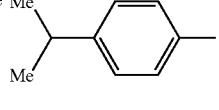 | Me | Me | — | + |
| 61b | Me | Me | Me, 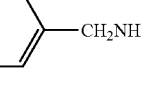 | Me | 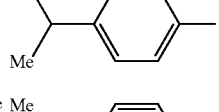 | Me | Me | — | + |
| 62b | Me | Me | Me, 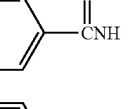 | Me | 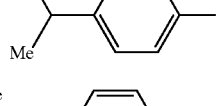 | Me | Me | — | − |
| 63b | Me | Me | Me, 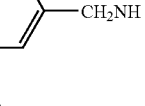 | Me | 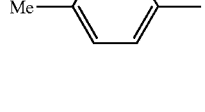 | Me | Me | — | − |
| 64b | Me | Me | 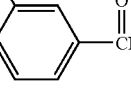 | Me | 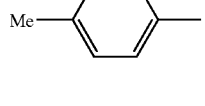 | Me | Me | — | |
| 65b | Me | Me | 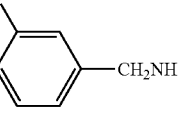 | Me | 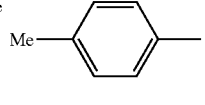 | Me | Me | — | |
| 66b | Me | Me | 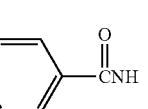 | Me | 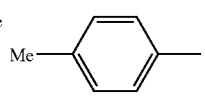 | Me | Me | — | |
| 67b | Me | Me | 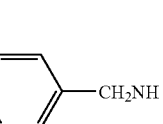 | Me | | Me | Me | — | |

As the compound (Ib), inter alia, preferred are:

(1) N-(4-fluorobenzyl)-2,2,4,6,7-pentamethyl-3-phenyl-2,3-dihydro-1-benzofuran-5-amine (Compound 4b) or a salt thereof, (2) N-benzyl-3-(4-isopropylphenyl)-2,2,4,6,7-pentamethyl-2,3-dihydro-1-benzofuran-5-amine (Compound 6b) or a salt thereof, (3) 3-(4-isopropylphenyl)-N-(4-methoxybenzyl)-N,2,2,4,6,7-hexamethyl-2,3-dihydro-1-benzofuran-5-amine (Compound 9b) or a salt thereof, (4) 3-(4-isopropylphenyl)-N-[2-(4-methoxyphenyl)ethyl]-2,2,4,6,7-pentamethyl-2,3-dihydro-1-benzofuran-5-amine (Compound 11b) or a salt thereof, (5) N-(4-fluorobenzyl)-3-(4-isopropylphenyl)-2,2,4,6,7-pentamethyl-2,3-dihydro-1-benzofuran-5-amine (Compound 19b) or a salt thereof, (6) N-(1,3-benzodioxol-5-ylmethyl)-3-(4-isopropylphenyl)-2,2,4,6,7-pentamethyl-2,3-dihydro-1-benzofuran-5-amine (Compound 23b) or a salt thereof, (7) N-(4-fluorobenzyl)-3-(4-fluorophenyl)-2,2,4,6,7-pentamethyl-2,3-dihydro-1-benzofuran-5-amine (Compound 31b) or a salt thereof, (8) N-(4-methoxybenzyl)-2,2,4,6,7-pentamethyl-3-(4-methylphenyl)-2,3-dihydro-1-benzofuran-5-amine (Compound 33b) or a salt thereof, (9) N-(4-fluorobenzyl)-2,2,4,6,7-pentamethyl-3-(4-methylphenyl)-2,3-dihydro-1-benzofuran-5-amine (Compound 35b) or a salt thereof,

(10) 3-(4-isopropylphenyl)-N-(4-methoxybenzyl)-2,4,6,7-tetramethyl-1-benzofuran-5-amine (Compound 45b) or a salt thereof,

(11) N-(4-fluorobenzyl)-3-(4-isopropylphenyl)-2,4,6,7-tetramethyl-1-benzofuran-5-amine (Compound 47b) or a salt thereof,

(12) N-(4-fluorobenzyl)-3-(4-fluorophenyl)-2,4,6,7-tetramethyl-1-benzofuran-5-amine (Compound 51b) or a salt thereof,

(13) N-(4-fluorobenzyl)-3-(4-isopropylphenyl)-1',4,6,7-tetramethylspiro[benzofuran-2(3H), 4'-piperidine]-5-amine (Compound 55b) or a salt thereof, and

(14) (R)-N-(4-fluorobenzyl)-3-(4-isopropylphenyl)-2,2,4,6,7-pentamethyl-2,3-dihydro-1-benzofuran-5-amine, hydrochloride thereof (Compound 61b) or other salts thereof, and more preferred are:

[1] N-(4-fluorobenzyl)-3-(4-isopropylphenyl)-2,2,4,6,7-pentamethyl-2,3-dihydro-1-benzofuran-5-amine (Compound 19b),

[2] N-(4-fluorobenzyl)-3-(4-isopropylphenyl)-1',4,6,7-tetramethylspiro[benzofuran-2(3H), 4'-piperidine]-5-amine (Compound 55b), and

[3] (R)-N-(4-fluorobenzyl)-3-(4-isopropylphenyl)-2,2,4,6,7-pentamethyl-2,3-dihydro-1-benzofuran-5-amine hydrochloride (Compound 61b).

In the compound (Ic), the group represented by the formula —X—$R^{4c}$ is preferably at the 5-position of the basic skeleton as follows:

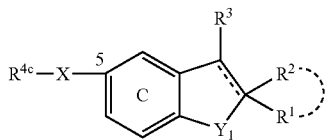

The compound (Ic) is preferably a compound in which $R^1$ and $R^2$ are each $C_{1-6}$ alkyl which may be optionally substituted with 1 to 3 substituents selected from (1) $C_{6-14}$ aryl, (2) $C_{1-6}$ alkoxy, (3) $C_{1-6}$ alkylthio, (4) hydroxy, (5) amino, (6) mono-$C_{1-6}$ alkylamino, (7) mono-$C_{6-14}$ arylamino, (8) di-$C_{1-6}$ alkylamino, (9) di-$C_{6-14}$ arylamino, (10) carboxy, (11) $C_{1-6}$ alkylsulfonyl, (12) $C_{6-14}$ arylsulfonyl, (13) $C_{1-6}$ alkylsulfinyl, (14) $C_{6-14}$ arylsulfinyl and (15) 5- to 7-membered saturated cyclic amino optionally substituted with 1 to 3 substituents selected from $C_{1-6}$ alkyl, $C_{6-14}$ aryl and 5- to 10-membered aromatic groups, or $R^1$ and $R^2$ are taken together with the adjacent carbon atom to form a 3- to 8-membered homocycle or heterocycle optionally substituted with 1 to 3 substituents selected from $C_{1-6}$ alkyl, $C_{6-14}$ aryl, $C_{7-16}$ aralkyl and 5- to 10-membered aromatic heterocyclic groups;

$R^3$ is phenyl, 1-naphthyl, 2-naphthyl, 2-thienyl, 3-thienyl, 2-pyridyl, 3-pyridyl, 4-pyridyl, 2-quinolyl, 3-quinolyl, 1-isoquinolyl, 1-indolyl, 2-indolyl or 2-benzothiazolyl each of which may be optionally substituted with 1 to 3 substituents selected from (1) halogen, (2) $C_{1-6}$ alkyl, (3) $C_{1-6}$ alkoxy, (4) amino, (5) mono-$C_{1-6}$ alkylamino, (6) di-$C_{1-6}$ alkylamino and (7) 5 to 7-membered saturated cyclic amino optionally substituted with 1 to 3 substituents selected from $C_{1-6}$ alkyl, $C_{6-14}$ aryl and 5- to 10-membered aromatic groups;

$R^{4c}$ is (i) $C_{1-6}$ alkyl substituted with phenyl, 1-naphthyl, 2-naphthyl, 2-thienyl, 3-thienyl, 2-pyridyl, 3-pyridyl, 4-pyridyl, 2-quinolyl, 3-quinolyl, 1-isoquinolyl, 1-indolyl, 2-indolyl or 2-benzothiazolyl each of which may be optionally substituted with 1 to 3 substituents selected from (1) halogen, (2) $C_{1-6}$ alkyl, (3) $C_{1-6}$ alkoxy, (4) hydroxy, (5) amino, (6) mono-$C_{1-6}$ alkylamino, (7) di-$C_{1-6}$ alkylamino, (8) carboxy and (9) 5- to 7-membered saturated cyclic amino optionally substituted with 1 to 3 substituents selected from $C_{1-6}$ alkyl, $C_{6-14}$ aryl and 5- to 10-membered aromatic groups, and optionally further substituted with carboxy or $C_{1-6}$ alkoxy-carbonyl, or (ii) $C_{1-6}$ alkyl-carbonyl, $C_{3-6}$ cycloalkyl-carbonyl, $C_{6-14}$ aryl-carbonyl or $C_{7-16}$ aralkyl-carbonyl each of which may be optionally substituted with 1 to 3 substituents selected from (1) halogen, (2) $C_{1-6}$ alkyl, (3) $C_{1-6}$ alkoxy, (4) hydroxy, (5) amino, (6) mono-$C_{1-6}$ alkylamino, (7) di-$C_{1-6}$ alkylamino and (8) carboxy;

X is an oxygen atom;

Y is an oxygen atom; and the $C^3$ ring is a benzene ring optionally further substituted with 1 to 3 substituents selected from halogen, optionally halogenated $C_{1-6}$ alkyl, optionally halogenated $C_{1-6}$ alkoxy, amino, mono-$C_{1-6}$ alkylamino and di-$C_{1-6}$ alkylamino.

More preferred is a compound in which $R^1$ and $R^2$ are each $C_{1-6}$ alkyl optionally substituted with 1 to 3 substituents selected from $C_{6-14}$ aryl, $C_{1-6}$ alkoxy, $C_{1-6}$ alkylthio, hydroxy, amino, mono-$C_{1-6}$ alkylamino, mono-$C_{6-14}$ arylamino, di-$C_{1-6}$ alkylamino, di-$C_{6-14}$ arylamino, carboxy, $C_{1-6}$ alkylsulfonyl, $C_{6-14}$ arylsulfonyl, $C_{1-6}$ alkylsulfinyl and $C_{6-14}$ arylsulfinyl, or $R^1$ and $R^2$ are taken together with the adjacent carbon atom to form piperidine optionally substituted with 1 to 3 substituents selected from $C_{1-6}$ alkyl, $C_{6-14}$ aryl and $C_{7-16}$ aralkyl;

$R^3$ is phenyl optionally substituted with 1 to 3 substituents selected from halogen, $C_{1-6}$ alkyl, $C_{1-6}$ alkoxy, amino, mono-$C_{1-6}$ alkylamino and di-$C_{1-6}$ alkylamino;

$R^4$ is (i) $C_{1-6}$ alkyl substituted with phenyl or pyridyl each of which may be optionally substituted with 1 to 3 substituents selected from halogen, $C_{1-6}$ alkyl, $C_{1-6}$ alkoxy, hydroxy, amino, mono-$C_{1-6}$ alkylamino, di-$C_{1-6}$ alkylamino and carboxy, or (ii) acyl represented by the formula —(C=O)—$R^{5'}$, wherein $R^{5'}$ is phenyl or phenyl-$C_{1-6}$ alkyl each of which may be optionally substituted with 1 to 3 substituents selected from halogen, $C_{1-6}$ alkyl, $C_{1-6}$ alkoxy, hydroxy, amino, mono-$C_{1-6}$ alkylamino, di-$C_{1-6}$ alkylamino and carboxy;

X is an oxygen atom;

Y is an oxygen atom; and the $C_3$ ring is a benzene ring optionally further substituted with 1 to 3 substituents selected from halogen, optionally halogenated $C_{1-6}$ alkyl, optionally halogenated $C_{1-6}$ alkoxy, amino, mono-$C_{1-6}$ alkylamino and di-$C_{1-6}$ alkylamino.

In addition, preferred is a compound represented by the formula:

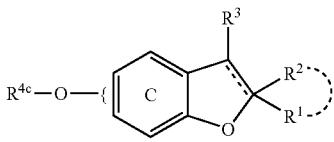

wherein $R^1$ and $R^2$ are each $C_{1-6}$ alkyl optionally substituted with phenyl-substituted 6-membered saturated cyclic amino, or $R^1$ and $R^2$ are taken together with the adjacent carbon atom to form piperidine substituted with $C_{1-6}$ alkyl or $C_{7-16}$ aralkyl;

$R^3$ is (i) a hydrogen atom, or (ii) phenyl optionally substituted with 1 to 3 substituents selected from (1) $C_{1-6}$ alkyl, (2) di-$C_{1-6}$ alkylamino and (3) 6-membered saturated cyclic amino optionally substituted with $C_{1-6}$ alkyl;

$R^{4c}$ is (i) phenyl optionally substituted with 1 to 3 substituents selected from nitro and $C_{1-6}$ alkyl-carboxamide, (ii) $C_{1-6}$ alkyl or $C_{2-6}$ alkenyl, each of which is substituted with 1 to 3 phenyl, quinolyl or pyridyl each of which may be optionally substituted with 1 to 3 substituents selected from $C_{1-6}$ alkoxy, $C_{1-6}$ alkylthio, $C_{1-6}$ alkoxy-carbonyl, $C_{1-6}$ alkylsulfonyl and $C_{1-6}$ alkylsulfinyl, and may be optionally further substituted with phenyl, carboxy or $C_{1-6}$ alkoxy-carbonyl, or (iii) acyl represented by the formula —(C=O)—$R^{5''}$, wherein $R^{5''}$ is phenyl substituted with $C_{1-6}$ alkoxy; and the C' ring is a benzene ring optionally further substituted with 1 to 3 $C_{1-6}$ alkyl (in particular, a benzene ring substituted with 3 $C_{1-6}$ alkyl such as methyl.

Specific examples of the compound (Ic) include preferably the following Compound 1c to 33c.

Compound 1c: 5-benzyloxy-3-(4-isopropylphenyl)-2,2,4,6,7-pentamethyl-2,3-dihydrobenzofuran Compound 2c: 5-benzyloxy-3-[4-(dimethylamino)phenyl]-2,2,4,6,7-pentamethyl-2,3-dihydrobenzofuran Compound 3c: 5-benzyloxy-2,4,6,7-tetramethyl-2-(4-phenyl-1-piperazinyl)methyl-2,3-dihydrobenzofuran Compound 4c: 3-(4-isopropylphenyl)-5-(4-methoxybenzyloxy)-2,2,4,6,7-pentamethyl-2,3-dihydrobenzofuran Compound 5c: 3-(4-isopropylphenyl)-5-(4-methoxybenzyloxy)-2,2-dimethyl-2,3-dihydrobenzofuran Compound 6c: 3-[4-(dimethylamino)phenyl]-5-(4-methoxybenzyloxy)-2,2,4,6,7-pentamethyl-2,3-dihydrobenzofuran Compound 7c: 5-(4-methoxybenzyloxy)-3-[4-(4-morpholinyl)phenyl]-2,2,4,6,7-pentamethyl-2,3-dihydrobenzofuran Compound 8c: 5-(4-methoxybenzyloxy)-2,2,4,6,7-pentamethyl-3-[4-(4-methyl-1-piperazinyl)phenyl]-2,3-dihydrobenzofuran Compound 9c: 3-(4-isopropylphenyl)-2,2,4,6,7-pentamethyl-5-(4-methylthiobenzyloxy)-2,3-dihydrobenzofuran Compound 10c: 3-(4-isopropylphenyl)-2,2,4,6,7-pentamethyl-5-[4-(methylsulfinyl)benzyloxy]-2,3-dihydrobenzofuran Compound 11c: 3-(4-isopropylphenyl)-2,2,4,6,7-pentamethyl-5-[4-(methylsulfonyl)benzyloxy]-2,3-dihydrobenzofuran Compound 12c: 3-(4-isopropylphenyl)-2,2,4,6,7-pentamethyl-5-(3-phenyl-2-propen-1-yloxy)-2,3-dihydrobenzofuran Compound 13c: 3-(4-isopropylphenyl)-2,2,4,6,7-pentamethyl-5-(2-quinolylmethyloxy)-2,3-dihydrobenzofuran hydrochloride Compound 14c: 5-(3,3-diphenylpropyloxy)-3-(4-isopropylphenyl)-2,2,4,6,7-pentamethyl-2,3-dihydrobenzofuran Compound 15c: methyl 4-[[3-(4-isopropylphenyl)-2,2,4,6,7-pentamethyl-2,3-dihydrobenzofuran-5-yl]oxymethyl]benzoate Compound 16c: methyl α-[[3-(4-isopropylphenyl)-2,2,4,6,7-pentamethyl-2,3-dihydrobenzofuran-5-yl]oxy]phenylacetate Compound 17c: 3-(4-isopropylphenyl)-2,2,4,6,7-pentamethyl-5-(2-pyridylmethyloxy)-2,3-dihydrobenzofuran Compound 18c: 3-(4-isopropylphenyl)-2,2,4,6,7-pentamethyl-5-(3-pyridylmethyloxy)-2,3-dihydrobenzofuran Compound 19c: 3-(4-isopropylphenyl)-2,2,4,6,7-pentamethyl-5-(4-pyridylmethyloxy)-2,3-dihydrobenzofuran Compound 20c: 3-(4-isopropylphenyl)-5-(2,4-dinitrophenyloxy)-2,2,4,6,7-pentamethyl-2,3-dihydrobenzofuran Compound 21c: 5-(2,4-bisacetylaminophenyloxy)-3-(4-isopropylphenyl)-2,2,4,6,7-pentamethyl-2,3-dihydrobenzofuran Compound 22c: α-[3-(4-isopropylphenyl)-2,2,4,6,7-pentamethyl-2,3-dihydrobenzofuran-5-yloxy]phenylacetic acid Compound 23c: α-[3-(4-isopropylphenyl)-2,2,4,6,7-pentamethyl-2,3-dihydrobenzofuran-5-yloxy]phenylacetic acid Compound 24c: 3-(4-isopropylphenyl)-2,2,4,6,7-pentamethyl-5-(3-phenyl-1-propyl)oxy-2,3-dihydrobenzofuran Compound 25c: 3-(4-isopropylphenyl)-2,2,4,6,7-pentamethyl-5-(2-phenylethyl)oxy-2,3-dihydrobenzofuran Compound 26c: 3-(4-isopropylphenyl)-2,4,6,7-tetramethylbenzofuran-5-yl 4-methoxybenzoate Compound 27c: 3-(4-isopropylphenyl)-5-(4-methoxybenzyloxy)-2,4,6,7-tetramethylbenzofuran Compound 28c: 2,4,6,7-tetramethyl-3-phenylbenzofuran-5-yl 4-methoxybenzoate Compound 29c: 3-(4-isopropylphenyl)-6-(4-methoxybenzyloxy)-2,2-dimethyl-2,3-dihydrobenzofuran Compound 30c: 1'-benzyl-3-(4-isopropylphenyl)-5-(4-methoxybenzyloxy)-4,6,7-trimethylspiro[benzofuran-2(3H), 4'-piperidine]

Compound 31c: 1'-benzyl-5-(4-methoxybenzyloxy)-4,6,7-trimethylspiro[benzofuran-2(3H), 4'-piperidine]

Compound 32c: 3-(4-isopropylphenyl)-5-(4-methoxybenzyloxy)-1',4,6,7-tetramethylspiro[benzofuran-2(3H), 4'-piperidine]

Compound 33c: 3-(4-isopropylphenyl)-1',4,6,7-tetramethyl-5-(4-pyridylmethyloxy)spiro[benzofuran-2(3H), 4'-piperidine]

The chemical structural formulas of Compounds 1c to 33c are shown below:

TABLE 8

[Benzofuran core structure with substituents labeled a, b (at 2-position), c (at 3-position), d (at 4-position), e (at 5-position), f (at 6-position), g (at 7-position)]

| Compound No. | a | b | c | d | e | f | g | = |
|---|---|---|---|---|---|---|---|---|
| 1c | Me | Me | 1-(4-methylphenyl)ethyl [Me-CH(Me)-C6H4-] | Me | PhCH2O- | Me | Me | — |
| 2c | Me | Me | 4-(N,N-dimethylamino)phenyl [Me2N-C6H4-] | Me | PhCH2O- | Me | Me | — |
| 3c | Me | 4-phenylpiperidin-1-ylmethyl [Ph-piperidine-N-CH2-] | H | Me | PhCH2O- | Me | Me | — |
| 4c | Me | Me | 1-(4-methylphenyl)ethyl | Me | 4-MeO-C6H4-CH2O- | Me | Me | — |
| 5c | Me | Me | 1-(4-methylphenyl)ethyl | H | 4-MeO-C6H4-CH2O- | H | H | — |
| 6c | Me | Me | 4-(N,N-dimethylamino)phenyl | Me | 4-MeO-C6H4-CH2O- | Me | Me | — |
| 7c | Me | Me | 4-(morpholin-4-yl)phenyl | Me | 4-MeO-C6H4-CH2O- | Me | Me | — |
| 8c | Me | Me | 4-(4-methylpiperazin-1-yl)phenyl | Me | 4-MeO-C6H4-CH2O- | Me | Me | — |
| 9c | Me | Me | 1-(4-methylphenyl)ethyl | Me | 4-MeS-C6H4-CH2O- | Me | Me | — |
| 10c | Me | Me | 1-(4-methylphenyl)ethyl | Me | 4-MeS(O)-C6H4-CH2O- | Me | Me | — |
| 11c | Me | Me | 1-(4-methylphenyl)ethyl | Me | 4-MeSO2-C6H4-CH2O- | Me | Me | — |
| 12c | Me | Me | 1-(4-methylphenyl)ethyl | Me | PhCH=CH-CH2O- | Me | Me | — |

TABLE 8-continued

| Compound No. | a | b | c | d | e | f | g | = |
|---|---|---|---|---|---|---|---|---|
| 13c | Me | Me | CH(Me)-C6H4- | Me | quinolin-2-yl-CH2O- | Me | Me | — |
| 14c | Me | Me | CH(Me)-C6H4- | Me | (Ph)2CH-CH2-CH2-O- | Me | Me | — |

TABLE 9

| Compound No. | a | b | c | d | e | f | g | = |
|---|---|---|---|---|---|---|---|---|
| 15c | Me | Me | CH(Me)-C6H4- | Me | MeOOC-C6H4-CH2O- | Me | Me | — |
| 16c | Me | Me | CH(Me)-C6H4- | Me | Ph-CH(COOMe)-O- | Me | Me | — |
| 17c | Me | Me | CH(Me)-C6H4- | Me | pyridin-2-yl-CH2O- | Me | Me | — |
| 18c | Me | Me | CH(Me)-C6H4- | Me | pyridin-3-yl-CH2O- | Me | Me | — |
| 19c | Me | Me | CH(Me)-C6H4- | Me | pyridin-4-yl-CH2O- | Me | Me | — |

TABLE 9-continued

| Compound No. | a | b | c | d | e | f | g | = |
|---|---|---|---|---|---|---|---|---|
| 20c | Me | Me | Me-CH(Me)-C6H4- | Me | 2,4-dinitro-methoxyphenyl | Me | Me | — |
| 21c | Me | Me | Me-CH(Me)-C6H4- | Me | 2,4-bis(NHAc)-methoxyphenyl | Me | Me | — |
| 22c | Me | Me | Me-CH(Me)-C6H4- | Me | Ph-CH(OMe)-COOH | Me | Me | — |
| 23c | Me | Me | Me-CH(Me)-C6H4- | Me | Ph-CH(OMe)-COOH | Me | Me | — |
| 24c | Me | Me | Me-CH(Me)-C6H4- | Me | Ph-CH2CH2CH2-OMe | Me | Me | — |
| 25c | Me | Me | Me-CH(Me)-C6H4- | Me | Ph-CH2CH2-OMe | Me | Me | — |
| 26c | Me | — | Me-CH(Me)-C6H4- | Me | MeO-C6H4-C(O)O- | Me | Me | = |
| 27c | Me | — | Me-CH(Me)-C6H4- | Me | MeO-C6H4-CH2O- | Me | Me | = |
| 28c | Me | — | Ph | Me | MeO-C6H4-C(O)O- | Me | Me | = |
| 29c | Me | Me | Me-CH(Me)-C6H4- | H | H | MeO-C6H4-CH2O- | H | — |

TABLE 10

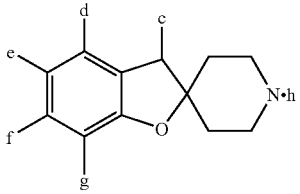

| Compound No. | c | d | e | f | g | h |
|---|---|---|---|---|---|---|
| 30c | Me-CH(Me)-C6H4- | Me | MeO-C6H4-CH2O- | Me | Me | -CH2-C6H5 |
| 31c | H | Me | MeO-C6H4-CH2O- | Me | Me | -CH2-C6H5 |
| 32c | Me-CH(Me)-C6H4- | Me | MeO-C6H4-CH2O- | Me | Me | Me |
| 33c | Me-CH(Me)-C6H4- | Me | Pyridyl-CH2O- | Me | Me | Me |

Inter alia, preferable Compound (Ic) includes:
3-(4-isopropylphenyl)-5-(4-methoxybenzyloxy)-2,2,4,6,7-pentamethyl-2,3-dihydrobenzofuran,
3-(4-methylphenyl)-2,4,6,7-tetramethylbenzofuran-5-yl 4-methoxybenzoate,
3-(4-isopropylphenyl)-2,4,6,7-tetramethylbenzofuran-5-yl 4-methoxybenzoate,
3-(4-isopropylphenyl)-5-(4-methoxybenzyloxy)-2,4,6,7-tetramethylbenzofuran,
3-(4-isopropylphenyl)-5-(4-methoxybenzyloxy)-1',4,6,7-tetramethylspiro[benzofuran-2(3H), 4'-piperidine],
3-(4-isopropylphenyl)-5-(3-pyridylmethyl)-2,2,4,6,7-pentamethyl-2,3-dihydrobenzofuran, and salts thereof.

Among them, particularly preferred are:
3-(4-isopropylphenyl)-5-(4-methoxybenzyloxy)-2,2,4,6,7-pentamethyl-2,3-dihydrobenzofuran,
3-(4-methylphenyl)-2,4,6,7-tetramethylbenzofuran-5-yl 4-methoxybenzoate,
3-(4-isopropylphenyl)-2,4,6,7-tetramethylbenzofuran-5-yl 4-methoxybenzoate,
3-(4-isopropylphenyl)-5-(4-methoxybenzyloxy)-2,4,6,7-tetramethylbenzofuran, and
3-(4-isopropylphenyl)-5-(4-methoxybenzyloxy)-1',4,6,7-tetramethylspiro[benzofuran-2(3H), 4'-piperidine] and salts thereof.

A salt of such a compound may be, for example, a metal salt, an ammonium salt or a salt with an organic base when the compound has an acidic group such as —COOH, or an inner salt such as a salt with an inorganic acid, an organic acid, or a basic or acidic amino acid when the compound has a basic group such as —NH2. Preferable examples of a metal salt include alkali metal salts such as a sodium salt or a potassium salt; alkaline earth metal salts such as a calcium salt, a magnesium salt or a barium salt; and an aluminum salt. Preferable examples of a salt with an organic base include salts with trimethylamine, triethylamine, pyridine, picoline, ethanolamine, diethanolamine, triethanolamine, dicyclohexylamine, and N,N-dibenzylethylenediamine. Preferable examples of a salt with an inorganic acid include salts with hydrochloric acid, hydrobromic acid, nitric acid, sulfuric acid and phospholic acid. Preferable examples of a salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Preferable examples of a salt with basic amino acid include salts with arginine, lysine and ornithine. Preferable examples of a salt with an acidic amino acid include salts with aspartic acid and glutamic acid.

Among them, pharmaceutically acceptable salts are preferable. Examples thereof include inorganic salts such as alkali metal salts (e.g. sodium salt, potassium salt etc.) or alkaline earth metal salts (e.g. calcium salt, magnesium salt, barium salt etc.) and an ammonium salt when the compound has an acidic functional group, and inorganic salts such as hydrochloride, sulfate, phosphate or hydrobromide and organic salts such as acetate, maleate, fumarate, succinate, methanesulfonate, p-toluenesulfonate, citrate or tartrate when the compound has a basic functional group.

The compound (I) (including the compounds (Ia), (Ib) and (Ic)) can be prepared by a method known per se, for example, a method described in WO 98/55454, WO 00/34262, WO 95/29907, JP-A 5-194466, U.S. Pat. No. 4,881,967, U.S. Pat. No. 4,212,865 or Tetrahedron Letters, vol. 37, No. 51, p. 9183-9186, 1996, or the similar method.

A prodrug of the compound (I) may be a compound which is converted into the compound (I) by a reaction with an enzyme or gastric acid under the physiological condition in vivo, that is, a compound which is changed into the compound (I) by enzymatic oxidation, reduction or hydrolysis or a compound which is changed into the compound (I) by hydrolysis with gastric acid or the like.

Examples of a prodrug of the compound (I) include a compound obtained by acylation, alkylation or phosphorylation of an amino group of the compound (I) (e.g. a compound obtained by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of an amino group of the compound (I)); a compound obtained by acylation, alkylation, phosphorylation or boration of a hydroxy group of the compound (I) (e.g. a compound obtained by acetylation, palmitoylation, propanoylation, pivaloylation, succinylation, fumarylation, alanylation or dimethylaminomethylcarbonylation of a hydroxy group of the compound (I)); and a compound obtained by esterification or amidation of a carboxyl group of the compound (I) (e.g. a compound obtained by ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl)methylesterification, cyclohexyloxycarbonylethylesterification or methylamidation of a carboxyl group of the compound (I)). These compounds can be prepared from the compound (I) by a method known per se.

Alternatively, the prodrug of the compound (I) may be a compound which is changed into the compound (I) under the physiological condition as described in "Development of medicines", vol. 7, Molecular Design, p. 163-198 published by Hirokawashoten in 1990.

The PKB activating agent of the present invention, inter alia, the compound (I) or a salt or a prodrug thereof (hereinafter, simply referred as Compound (I) collectively in some cases) leads to nerve degeneration inhibiting effect, nerve regeneration promoting effect, neural stem cell self-replication promoting effect, stem cell (e.g. embryonic stem cell, neural stem cell etc.) proliferation promoting effect, or neural precursor cell differentiation promoting effect by activating PKB, or leads to medical effect such as neural stem cell self-replication promoting effect, stem cell (e.g. embryonic stem cell, neural stem cell etc.) proliferation promoting effect, neural precursor cell differentiation promoting effect, neurotrophic factor-like effect, neurotrophic factor activity enhancing effect, nerve degeneration inhibiting effect, nerve regeneration promoting effect, or neural cell death inhibiting effect by antioxidative effect or β amyloid, through the information transmission of inhibiting GSK as a substrate of PKB, in a mammal (e.g. mouse, rat, hamster, rabbit, cat, dog, bovine, sheep, monkey, human etc.); and thus, it is expected to prevent and/or treat Parkinson's disease and Alzheimer's disease. Since the PBK activating agent of the present invention, inter alia, Compound (I) has excellent nature as a medicine such as low toxicity and little side effect, it is useful as an agent for preventing or treating Parkinson's disease and Alzheimer's disease.

The PKB activating agent of the present invention is also useful as an agent for preventing or treating depression (particularly preferably, depression accompanied with atrophy or deficiency of nerve), anxiety, manic-depressive psychosis or PTSD. Inter alia, it is particularly useful for depression accompanied with atrophy or deficiency of nerve. In addition, it is also effective against cognition impairment accompanied with depression. Inter alia, Compound (I) is useful for treating or preventing these disorders.

In addition to prevention or treatment of Parkinson's disease, Alzheimer's disease, depression, anxiety, manic-depressive psychosis or PTSD, a medicine containing the PKB activating agent including Compound (I) is also effective against other diseases such as neurodegenerative disease (e.g. mild cognition impairment (MCI), amyotrophic lateral sclerosis (ALS), Huntington's disease, spinocerebellar degenerative disease, multiple sclerosis (MS), Pick's disease etc.), other mental disease (e.g. schizophrenia, anxiety neurosis, obsessive-compulsive neurosis etc.), head trauma, spinal cord injury, cerebrovascular disorder, cerebrovascular dementia, asymptomatic brain infarction, polyglutamine disease (dentatorubral-pallidoluysian atrophy, bulbospinal muscular atrophy, Machado-Jacob disease, spinocerebellar ataxia type 6), prion disease (Creutzfeldt-Jacob disease, Gerstmann-straussler-Scheinker disease), corticobasal ganglionic degeneration, progressive supranuclear palsy, AIDS encephalopathy, muscular dystrophy, diabetic neuropathy, and the like by inhibiting nerve cell death and promoting regeneration of neural tissue or function by neurotization and neural axon extension as a proliferation and/or differentiation promoting agent for a stem cell and/or neural precursor cell or as a neurotrophic factor-like substance, a neurotrophic factor activity enhancing substance or a nerve degeneration inhibiting substance; and thus it may be used as an agent for preventing or treating these diseases, together with or independent of prevention or treatment of Parkinson's disease, depression, anxiety, manic-depressive psychosis or PTSD.

A medicine containing the PKB activating agent including Compound (I) also has differentiation-promoting effect on various stem cell systems and thereby can activate endogenous self-regenerating ability and promote regeneration of the tissue or function of pancreatic β-cells, hepatic cells, osteoblasts or the like; and thus it can be used as, for example, an agent for preventing or treating diabetic retinopathy, diabetic nephropathy, liver cirrhosis, alcoholic hepatitis, or various senile diseases accompanied with decrease in self-regenerating ability; an osteogenesis promoting agent, a bone disease preventing or treating agent, a fracture preventing or treating agent, a chondrogenesis promoting agent or a chondropathy preventing or treating agent (e.g. non-metabolic bone disease [e.g. fracture, re-fracture, bone deformation-spondylosis deformans, osteosarcoma, myeloma, osteogenesis imperfecta, scoliosis etc. in the orthopedic field], metabolic bone disease [e.g. bone defect, osteoporosis, osteomalacia, rickets, osteitis fibrosa, renal osteodystrophy, bone Paget's disease, rigid myelitis etc.], joint disease [e.g. a preventing or treating drug of chondropathy such as osteoarthritis and rheumatoid arthritis]; as well as a bone tissue repairing agent after a surgical operation for multiple myeloma, lung cancer, breast cancer or the like. In the dental field, a medicine containing the PKB activating agent including Compound (I) can be also used for treating periodontal disease, repairing periodontal tissue defect caused by periodontal disease, stabilizing a dental implant, forming alveolar ridge or repairing cleft palate.

The PKB activating agent such as Compound (I) can be safely administered orally or parenterally (e.g. locally, rectally, venously etc.), as it is or as a pharmaceutical composition, for example, a tablet (including a sugar-coated tablet, a film coated tablet, an orally disintegrating tablet etc.), powder, a granule, a capsule (including a soft capsule), liquid, injection, a suppository, a sustained-release preparation and a patch, produced by mixing with a pharmacologically acceptable carrier according to a per se known means.

The content of Compound (I) in the preparation of the present invention is, for example, about 0.01 to about 100% by weight of the whole preparation.

The dose varies depending on an administration subject, an administration route, disease and the like. For example, when Compound (I) is orally administered to an adult as a Parkinson's disease treating agent, the compound of the present invention as an active ingredient may be administered in an amount of about 0.1 to about 20 mg/kg body weight, preferably about 0.2 to about 10 mg/kg body weight, further preferably about 0.5 to about 10 mg/kg body weight, preferably about 0.5 to about 5 mg/kg body weight. The dose may be administered in one or several divided portions per day.

When the PKB activating agent such as Compound (I) is used for treating or preventing Parkinson's disease, Alzheimer's disease, depression, anxiety, manic-depressive psychosis or PTSD, or applied to treatment or prevention of the above-mentioned disease such as neurodegenerative disease (e.g. Alzheimer's disease, Parkinson's disease, amyotrophic lateral sclerosis (ALS), Huntington's disease, spinocerebellar degenerative disease, multiple sclerosis (MS), etc.), psychoneurotic disease (e.g. schizophrenia, etc.), head trauma, spinal cord injury, cerebrovascular disorder, cerebrovascular dementia, spinal cord injury polyglutamine disease (dentatorubral-pallidoluysian atrophy, bulbospinal muscular atrophy, Machado-Jacob disease, spinocerebellar ataxia type 6), prion disease (Creutzfeldt-Jacob disease, Gerstmann-straussler-Scheinker disease), corticobasal ganglionic degeneration, progressive supranuclear palsy, AIDS encephalopathy, muscular dystrophy, diabetic neuropathy, diabetic retinopathy, diabetic nephropathy, liver cirrhosis, alcoholic hepatitis or osteoporosis, together with or independent of the treatment of Parkinson's disease, Alzheimer's disease, depression, anxiety, manic-depressive psychosis or PTSD; the PKB activating agent such as Compound (I) may be used in combination with another active ingredient. Examples of such a concomitant drug include an acetylcholinesterase inhibitor (e.g. donepezil, rivastigmine, galantamine, zanapezil (TAK-147) etc.), a β-amyloid protein production, secretion, accumulation, aggregation and/or deposition inhibitor [a β-secretase inhibitor (e.g. 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl)methoxyteralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO 01/00663)), a γ-secretase inhibitor, a β-amyloid protein aggregation inhibitor (e.g. PTI-00703, ALZHEMED (NC-531), PPI-368 (JP-A 11-514333), PPI-558 (JP-A 2001-500852), SKF-74652 (Biochem. J. (1999), 340(1), 283-289)), β-amyloid vaccine, β-amyloid degrading enzyme etc.], a brain function activating agent (e.g. aniracetam, nicergoline etc.), other Parkinson's Disease treating drugs [(e.g. dopamine receptor agonist (L-dopa, Bromocriptine, pergolide, talipexole, pramipexole, cabergoline, adamantadine etc.), a monoamine oxidase (MAO) inhibitor (deprenyl, selegiline, remacemide, riluzole etc.), an anti-choline agent (e.g. trihexyphenidyl, biperidene etc.), a COMT inhibitor (e.g. entacapone etc.)], an amyotrophic lateral sclerosis treating drug (e.g. riluzole etc., neurotrophic factor etc.), a hyperlipemia treating drug such as a cholesterol lowering drug [statin series (e.g. sodium pravastatin, atorvastatin, simvastatin, rosuvastatin etc.), fibrate (e.g. clofibrate etc.), a squalene synthase inhibitor], a drug for treating abnormal behavior or dromomania accompanied with progression of dementia (e.g. sedative, anti-anxiety drug etc.), an apoptosis inhibitor (e.g. CPI-1189, IDN-6556, CEP-1347 etc.), a nerve differentiation/regeneration promoting agent (leteprinim, xaliproden (SR-57746-A), SB-216763 etc.), a hypotensive drug, a diabetes treating drug, an antidepressant, an antianxiety drug, a non-steroidal anti-inflammatory drug (e.g. meloxicam, tenoxicam, indomethacin, ibuprofen, celecoxib, rofecoxib, aspirin, indomethacin etc.), a disease modifying anti-rheumatoid drug (DMARD), an anti-cytokine drug (e.g. TNF inhibitor, MAP kinase inhibitor etc.), a steroid drug (e.g. dexamethasone, hexestrol, cortisone acetate etc.), sex hormone or a derivative thereof (e.g. progesterone, estradiol, estradiol benzoate etc.), parathyroid hormone (PTH), and a calcium receptor antagonist. Inter alia, it is preferable to use in combination with a β-secretase inhibitor such as 6-(4-biphenylyl)methoxy-2-[2-(N,N-dimethylamino)ethyl]tetralin hydrochloride monohydrate.

Such another active ingredient and the PKB activating agent, the agent for preventing or treating Parkinson's disease, Arzheimer's disease, depression or the like, including Compound (I) of the present invention may be mixed according to a known per se method to be formulated into one pharmaceutical composition (e.g. a tablet, powder, a granule, a capsule (including a soft capsule), liquid, a injection, a suppository, a sustained-release preparation etc.), or they may be formulated into separate compositions and then administered to the same subject simultaneously or at a certain interval.

A pharmacologically acceptable carrier which may be used for preparing the preparation of the present invention includes various organic or inorganic carrier substances which are conventional as a drug formulation material, for example, excipients, lubricants, binders and disintegrants for a solid preparation; and solvents, solubilizers, suspending agents, isotonizing agents, buffering agents and soothing agents for a liquid preparation. If necessary, conventional additives such as preservatives, anti-oxidants, coloring agents, sweeteners, adsorbents and wetting agents may be used.

Examples of excipients include lactose, white sugar, D-mannitol, starch, corn starch, crystalline cellulose and light anhydrous silicic acid.

Examples of lubricants include magnesium stearate, calcium stearate, talc and colloidal silica.

Examples of binders include crystalline cellulose, white sugar, D-mannitol, dextrin, hydroxypropylcellulose, hydroxypropylmethylcellulose, polyvinylpyrrolidone, starch, sucrose, gelatin, methylcellulose, and carboxymethylcellulose sodium.

Examples of disintegrants include starch, carboxymethylcellulose, carboxymethylcellulose calcium, croscarmellose sodium, sodium carboxymethyl starch and L-hydroxypropylcellulose.

Examples of solvents include water for injection, alcohol, propylene glycol, macrogol, sesame oil, corn oil and olive oil.

Examples of solubilizers include polyethylene glycol, propylene glycol, D-mannitol, benzyl benzoate, ethanol, trisaminomethane, cholesterol, triethanolamine, sodium carbonate, and sodium citrate.

Examples of suspending agents include surfactants such as stearyltriethanolamine, sodium lauryl sulfate, laurylaminopropionic acid, lecithin, benzalkonium chloride, benzethonium chloride and glycerin monostearate; and hydrophilic polymers such as polyvinyl alcohol, polyvinylpyrrolidone, sodium carboxymethylcellulose, methylcellulose, hydroxymethylcellulose, hydroxyethylcellulose and hydroxypropylcellulose.

Examples of isotonizing agents include glucose, D-sorbitol, sodium chloride, glycerin and D-mannitol.

Examples of buffering agents include buffer solutions of phosphate, acetate, carbonate, citrate, and the like.

Examples of soothing agents include benzyl alcohol.

Examples of preservatives include parahydroxybenzoic acid esters, chlorobutanol, benzyl alcohol, phenethyl alcohol, dehydroacetic acid and sorbic acid.

Examples of antioxidants include sulfite, ascorbic acid and α-tocopherol.

EXAMPLES

The following Preparation and Experimental Examples explain the present invention in detail, but they are merely examples and not intended to limit the present invention. They may be varied within the scope of the present invention.

Preparation Example 1a

| | |
|---|---|
| (1) Compound 14a | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Carboxymethylcellulose calcium | 20 mg |
| Total | 120 mg |

According to a conventional method, the above (1) to (6) are mixed and compressed into a tablet with a tableting machine.

Preparation Example 1b

| | |
|---|---|
| (1) Compound 19b | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Carboxymethylcellulose calcium | 20 mg |
| Total | 120 mg |

According to a conventional method, the above (1) to (6) are mixed and compressed into a tablet with a tableting machine.

Preparation Example 1c

| | |
|---|---|
| (1) Compound 4c | 50 mg |
| (2) Lactose | 34 mg |
| (3) Corn starch | 10.6 mg |
| (4) Corn starch (paste) | 5 mg |
| (5) Magnesium stearate | 0.4 mg |
| (6) Carboxymethylcellulose calcium | 20 mg |
| Total | 120 mg |

According to a conventional method, the above (1) to (6) were mixed and compressed into a tablet with a tableting machine.

Experimental Example 1

Experimental Method

The hippocampus was removed from a 3 day-old rat and the cells were dispersed in a nerve dispersing solution. After the number of the cells was counted, the cells were suspended in a DMEM/F-12 medium containing 10% FCS (Embryo Max) and was then seeded on a 6-well plate coated with type I collagen at a density of $3\times10^5$ cells/cm$^2$. After cultured for 4 days, the medium was replaced with a N2 supplement-containing medium. Compound (I) (Compound 17a was used; hereinafter referred to Compound A) was added to a well at 300 nM or 100 nM, and IGF-1 was added to a well at 100 ng/mL. One day or three days after the addition, the cells were collected using Lysis Buffer containing protease inhibitor cocktail. Each cell suspension was centrifuged at 20000 rpm for 30 minutes and the supernatant was collected. An anti-5G3 Akt antibody was added to the supernatant to immunoprecipitate intracellular Akt. The resulting precipitate was subjected to SDS-PAGE using a 5-20% polyacrylamide gel and then to Western blotting. An anti-Phospho Akt antibody as a primary antibody and an HRP-linked anti-Rabbit antibody as a secondary antibody were used to detect the bands of phosphorylated Akt (Ser473 and Thr308). In order to detect the total Akt, the PVDF membrane was immersed in a reprobe buffer and permeated at 55° C. for 20 minutes to peel the antibodies. After that, an anti-Akt antibody (Cell signaling technology) as a primary antibody and an HRP-linked anti-Rabbit antibody (Cell signaling technology) as a secondary antibody were used to detect the band of total Akt.

Results of Experiment

Effect of Compound A on Phosphorylation of Akt in a Rat Hippocampus Mixed Culturing System Effects of Compound A and insulin-like growth factor-1 (IGF-1) are shown in FIG. 1. The addition of Compound A promoted phosphorylation at both Thr308 and Ser473 sites after one day and three days (FIG. 1). The addition of 100 ng/mL of IGF-1 also promoted phosphorylation of Thr308 and Ser473. From these results, it was revealed that Compound A has Akt activating effect.

INDUSTRIAL APPLICABILITY

Entirely unlike previous replacement therapy with dopamine or the like, the PKB activating agent of the present invention is useful for preventing or treating Parkinson's disease by more fundamentally promoting endogenous proliferation or differentiation of nerve stem cells or by promoting engraftment or differentiation in a nerve stem cell or nerve cell transplantation.

In addition, the PKB activating agent of the present invention, inter alia, the PKB activating agent containing Compound (I) or a salt or a prodrug thereof, and a nerve regeneration promoting agent based on the PKB activation have medical effects such as neural stem cell self-replication promoting effect, neural precursor cell differentiation promoting effect, neurotrophic factor-like effect, neurotrophic factor activity enhancing effect, nerve degeneration inhibiting effect, nerve regeneration promoting effect, and neural cell death inhibiting effect by antioxidative effect or β amyloid, which lead to inhibiting atrophy of pyramidal cells in the CA3 region of hippocampus, preventing suppression of nerve neogenesis in hippocampus caused by stress, or promoting nerve neogenesis or differentiation in hippocampus; and therefore are useful as an agent for preventing or treating depression, anxiety, manic-depressive psychosis or PTSD. From these findings, the agent of the present invention is also effective as a treating drug of cognition impairment accompanied with depression.

The invention claimed is:

1. A method for treating depression in a human, which comprises administering a protein kinase B activating agent comprising (R)-5,6-dimethoxy-2-[2,2,4,6,7-pentamethyl-3-(4-methylphenyl)-2,3-dihydro-1-benzofuran-5-yl]isoindoline, or a salt thereof to the human, wherein the human is not a human with schizophrenia.

* * * * *